US011432931B2

(12) United States Patent
Lang

(10) Patent No.: US 11,432,931 B2
(45) Date of Patent: *Sep. 6, 2022

(54) ARTIFICIAL NEURAL NETWORK FOR FITTING OR ALIGNING ORTHOPEDIC IMPLANTS

(71) Applicant: Philipp K. Lang, Franconia, NH (US)

(72) Inventor: Philipp K. Lang, Franconia, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,810

(22) Filed: Jan. 14, 2022

(65) Prior Publication Data

US 2022/0133484 A1 May 5, 2022

Related U.S. Application Data

(63) Continuation of application No. 16/268,793, filed on Feb. 6, 2019, now Pat. No. 11,278,413.

(60) Provisional application No. 62/626,712, filed on Feb. 6, 2018.

(51) Int. Cl.
*A61F 2/30* (2006.01)
*A61F 2/32* (2006.01)
*A61F 2/38* (2006.01)
*A61F 2/40* (2006.01)
*G16H 30/40* (2018.01)
*A61F 2/42* (2006.01)

(52) U.S. Cl.
CPC ............ *A61F 2/30942* (2013.01); *A61F 2/32* (2013.01); *A61F 2/38* (2013.01); *A61F 2/40* (2013.01); *A61F 2/4202* (2013.01); *G16H 30/40* (2018.01); *A61F 2002/30943* (2013.01); *A61F 2002/30948* (2013.01); *A61F 2002/30952* (2013.01)

(58) Field of Classification Search
CPC ... A61B 2034/108; A61B 34/10; A61B 34/00; A61F 2/30942; A61F 2/32; A61F 2/38; A61F 2/40

See application file for complete search history.

(56) References Cited

U.S. PATENT DOCUMENTS 9,861,446 B2    1/2018  Lang

OTHER PUBLICATIONS

Bonnin, et al., "Mediolateral oversizing influences pain, function, and flexion after TKA", Knee Surg. Sports Traumatol Arthrosc, vol. 21, pp. 2314-2324, (2013).
Gromov, et al., "What is the optimal alignment of the tibial and femoral components in knee arthroplasty?", Acta Orthopaedica, vol. 85, No. 5, pp. 480-487, Sep. 2014.
Kawahara, et al., "A lateralized anterior flange improves femoral component bone coverage in current total knee prostheses", The Knee, vol. 23, pp. 719-724, (2016).
Mahoney, et al., "Overhang of the Femoral Component in Total Knee Arthroplasty: Risk Factors and Clinical Consequences", The Journal of Bone and Joint Surgery, Incorporated, vol. 92-A, No. 5, pp. 1115-1121, May 2010.
Schroeder, et al., "In Vivo Tibial Fit and Rotational Analysis of a Customized, Patient-Specific TKA versus Off-the-Shelf TKA", The Journal of Knee Surgery, vol. 32, No. 06, pp. 499-505, (2019).

*Primary Examiner* — Jason-Dennis N Stewart
(74) *Attorney, Agent, or Firm* — Greenberg Traurig, LLP; Natalie Salem; Barry Schindler

(57) ABSTRACT

Devices, systems, techniques and methods for determining the fit of an implant and for determining one or more prognosticators, indicators or risk factors of postoperative performance are provided.

27 Claims, No Drawings

ARTIFICIAL NEURAL NETWORK FOR FITTING OR ALIGNING ORTHOPEDIC IMPLANTS

RELATED APPLICATIONS

This application is a continuation application of U.S. application Ser. No. 16/268,793, filed Feb. 6, 2019, which claims the benefit of and priority to U.S. Provisional Application Ser. No. 62/626,712, filed Feb. 6, 2018, the entire contents of each of which are hereby incorporated by reference in their entireties.

TECHNICAL FIELD

Aspects of the present disclosure provide for systems and methods to determine the fit, size and/or shape of a knee, hip, shoulder, ankle joint replacement or other orthopedic implant.

BACKGROUND

Most knee, hip, shoulder and/or ankle replacement or other orthopedic implants are provided in a limited number of sizes and shapes which can make the fit to the patient's joint challenging.

SUMMARY

Various embodiments of the present disclosure relate to systems and methods for determining the fit of a virtual implant component for a joint replacement in a patient. In some embodiments, the system comprises at least one computer system comprising at least one processor, wherein the at least one processor is configured to receive imaging data from the patient undergoing joint replacement, wherein the at least one computer processor is configured to derive at least one anatomic structure of the patient from the imaging data, wherein the at least one processor is configured to align the virtual implant component in relationship to at least one of a mechanical axis, a rotation axis, a transepicondylar axis, a Whiteside's line, a femoral bone surface, a femoral condyle surface, a femoral offset, a femoral component flexion, an anterior cortex, a tibial plateau surface, a tibial slope, a medial joint line, a lateral joint line, or combinations thereof, and wherein the at least one processor is configured to determine the fit of the virtual implant component in relationship to the at least one anatomic structure.

In some embodiments, the at least one anatomic structure comprises at least one of a peripheral margin, a dimension, a shape, a radius, a convexity, or a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau surface, a lateral tibial plateau surface, a medial tibial plateau surface, a lateral tibial plateau surface, a femoral offset, a tibial plateau offset, any of the foregoing structures on a surgically exposed surface, any of the foregoing structures in a subsurface location or combinations thereof.

In some embodiments, the at least one processor is configured to determine an overhang or an oversizing of the virtual implant component in relationship to at least one of a peripheral margin, a dimension, a shape, a radius, a convexity, or a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, any of the foregoing structures in a subsurface location or combinations thereof.

In some embodiments, the at least one processor is configured to determine an undersizing of the virtual implant component in relationship to at least one of a peripheral margin, a dimension, a shape, a radius, a convexity, or a concavity of at least one of a medial wall of the femoral notch, a lateral wall of the femoral notch; a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, any of the foregoing structures in a subsurface location or combinations thereof.

In some embodiments, the at least one processor is configured to use a single parameter or multiple parameters for determining the fit of the virtual implant component.

In some embodiments, the at least one processor is configured to use a single parameter or multiple parameters for aligning the virtual implant component. In some embodiments, the single or multiple parameters comprise at least one of a mechanical axis, a rotation axis, a transepicondylar axis, a Whiteside's line, a tibial slope, a femoral offset, a femoral component flexion, an anterior notching, an anterior cortex, a medial joint line, a lateral joint line or combinations thereof.

In some embodiments, the at least one anatomic structure is derived from at least one of a CT scan, MRI scan, ultrasound scan, data generated based on one, two or more x-rays, or combinations thereof.

In some embodiments, the joint is a hip joint and the at least one processor is configured to determine the fit of the virtual implant component in relationship to at least one of a peripheral margin, a dimension, a shape, a radius, a convexity, or a concavity of at least one of a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a fovea capitis, a transverse acetabular ligament, a pulvinar, a ligamentum teres, a labrum, one or more osteophytes or combinations thereof.

In some embodiments, the joint is a shoulder joint and the at least one processor is configured to determine the fit of the virtual implant component in relationship to at least one of a peripheral margin, a dimension, a shape, a radius, a convexity, or a concavity of at least one of a portion or an entire glenoid; a portion or an entire coracoid process, a portion or an entire acromion, a portion of a clavicle, a portion or an entire humeral head, a portion or an entire humeral neck, a portion of a humeral shaft, one or more humeral osteophytes, one or more glenoid osteophytes, a portion or an entire glenoid labrum, a portion or an entire shoulder ligament, a portion of a shoulder capsule, or combinations thereof.

In some embodiments, the at least one processor is configured to select at least one virtual implant component from a library of virtual implant components. In some embodiments, the library of virtual implant components comprises at least two virtual implant components, wherein the at least two virtual implant components have different sizes. In some embodiments, the library of virtual implant components comprises at least two virtual implant components, wherein at least two virtual implant components have different shapes. In some embodiments, the shapes are symmetric. In some embodiments, the shapes are asymmetric. In some embodiments, the virtual implant components are stored in STL file format in the library of virtual implant components.

In some embodiments, the at least one processor is configured to determine the fit of the virtual implant component using an artificial neural network. In some embodiments, the artificial neural network is a discriminative artificial neural network or a generative neural network.

In some embodiments, the at least one processor is configured to determine a score of implant oversizing or overhang or of implant undersizing in relationship to the one or more anatomic landmark. In some embodiments, the anatomic structure comprises at least one of an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface or combinations thereof.

In some embodiments, the at least one processor is configured to compute a risk of developing postoperative pain based on the score. In some embodiments, the at least one processor is configured to determine the fit as a virtual implant component overhang, virtual implant component oversizing, a virtual implant component undersizing or combinations thereof and wherein the at least one processor is configured to determine the virtual implant component overhang, virtual implant component oversizing, virtual implant component undersizing or combinations thereof in numeric values and wherein the numeric values comprise at least one of mm, $mm^2$, $mm^3$ or combinations thereof.

Some embodiments relate to a system for preparing a physical joint for a joint replacement in a patient comprising at least one computer system comprising at least one processor, wherein the at least one processor is configured to receive preoperative data, intraoperative data, or preoperative and intraoperative data of the patient undergoing joint replacement from one or more data sources, wherein the preoperative data, intraoperative data, or preoperative and intraoperative data are based on imaging data, wherein the at least one processor is configured to compare at least one size, shape or combinations thereof of a virtual implant component with the preoperative data, intraoperative data, or preoperative and intraoperative data, and wherein the at least one processor is configured to select at least one size, shape, or combinations thereof, of a virtual implant component based on the size, fit, shape or combinations thereof of the virtual implant component and based on the preoperative, intraoperative or preoperative and intraoperative data.

In some embodiments, the at least one processor uses a single parameter or multiple parameters for the comparing and wherein the parameter is based on or derived from the preoperative data, intraoperative data, or preoperative and intraoperative data.

In some embodiments, the preoperative data, intraoperative data, or preoperative and intraoperative data are comprised of the imaging data.

In some embodiments, the imaging data are comprised of at least one of a CT scan, MRI scan, ultrasound scan, or data generated based on one, two or more x-rays.

In some embodiments, the single or multiple parameters comprise at least one of a mechanical axis, a rotation axis, a transepicondylar axis, a Whiteside's line, a tibial slope, a femoral offset, a tibial offset, a femoral component flexion, an anterior cortex, a medial joint line, a lateral joint line, a tibial offset or combinations thereof.

In some embodiments, the at least one processor is configured to align the virtual implant component in relationship to at least one of a mechanical axis, a rotation axis, a transepicondylar axis, a Whiteside's line, a femoral bone surface, a femoral condyle surface, a femoral offset, a femoral component flexion, an anterior cortex, a tibial plateau surface, a tibial slope, a tibial offset, a medial joint line, a lateral joint line or combinations thereof.

In some embodiments, the joint is a knee joint and the single or multiple parameters comprise at least one of a coordinate, a peripheral margin, a dimension, a shape, a radius, a convexity, a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau surface, a lateral tibial plateau surface, a medial tibial plateau surface, a lateral tibial plateau surface, any of the foregoing tissues and/or structures on a surgically exposed surface, any of the foregoing tissues and/or structures in a subsurface location, or combinations thereof.

In some embodiments, the joint is a hip joint and the single or multiple parameters comprise at least one of a coordinate, a peripheral margin, a dimension, a shape, a radius, a convexity, or a concavity of at least one of a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a fovea capitis, a transverse acetabular ligament, a pulvinar, a ligamentum teres, a labrum, one or more osteophytes or combinations thereof.

In some embodiments, the joint is a shoulder joint and the single or multiple parameters comprise at least one of a coordinate, a peripheral margin, a dimension, a shape, a radius, a convexity, or a concavity of at least one of a portion or an entire glenoid, a portion or an entire coracoid process, a portion or an entire acromion, a portion of a clavicle, a portion or an entire humeral head, a portion or an entire humeral neck, a portion of a humeral shaft, one or more humeral osteophytes, one or more glenoid osteophytes, a portion or an entire glenoid labrum, a portion or an entire shoulder ligament, a portion of a shoulder capsule or combinations thereof. In some embodiments, the at least one processor is configured to select the virtual implant from a library of virtual implant components. In some embodiments, the library of virtual implant components comprises at least two or more virtual implant components, wherein the two or more virtual implant components have different sizes. In some embodiments, the library of virtual implant components comprises at least two or more virtual implant components, wherein the two or more virtual implant components have different shapes. In some embodiments, the shapes are symmetric. In some embodiments, the shapes are asymmetric. In some embodiments, the virtual implant components are stored in STL file format in the library of virtual implant components.

In some embodiments, the at least one processor is configured to determine the fit of the virtual implant component in relationship to the preoperative data, intraoperative data, or preoperative and intraoperative data.

In some embodiments, the at least one processor is configured to determine the fit of the virtual implant component in relationship to at least one of a peripheral margin, a dimension, a shape, a radius, a convexity, or a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, any of the foregoing structures in a subsurface location or combinations thereof.

In some embodiments, the at least one processor is configured to determine an overhang or an oversizing of the virtual implant component in relationship to at least one of a peripheral margin, a dimension, a shape, a radius, a convexity, or a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, any of the foregoing structures in a subsurface location or combinations thereof.

In some embodiments, the computer processor is configured to determine an undersizing of the virtual implant component in relationship to at least one of a peripheral margin, a dimension, a shape, a radius, a convexity, or a concavity of at least one of a medial wall of the femoral notch, a lateral wall of the femoral notch; a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, any of the foregoing structures in a subsurface location or combinations thereof.

In some embodiments, the at least one processor is configured to select at least one size or shape of a virtual implant component using an artificial neural network. In some embodiments, the artificial neural network is a discriminative artificial neural network or a generative neural network.

DETAILED DESCRIPTION

Current techniques do not allow to assess the fit, size or shape of implants or implant components pre-operatively to derive, for example, an assessment of implant overhang, oversizing and/or undersizing and, for example, to determine a risk of developing postoperative pain or complications.

Many different computer languages can be used to execute some of the functions described in the specification. These include computer languages, e.g. Fortran, Pascal, C, C++, C--, Basic and many others known in the art.

In some embodiments, voice commands, hand commands, gesture commands, keyboard commands, track pad commands, mouse commands, graphical user interface commands and any other command input device known in the art.

Artificial Intelligence

Various embodiments of the present disclosure can use one or more artificial intelligence systems, techniques and/or methods (AI), including, for example, neural networks (e.g. deep learning), algorithms, machine learning, statistical analysis and analytics (e.g. regression), predictive analytics, nearest neighbor algorithms, support vector machines, segmentation and segmentation algorithms, classification systems, techniques and methods, or other algorithms, methods, techniques or systems to develop predictive or recommend treatment and/or behavioral modifications. AI including systems, techniques and/or methods including machine learning and iterative learning can include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

AI can, for example, be trained on and work with data related to objects, relations between objects, properties and categories and modify clinical decisions and/or behavior. A set of objects, relations between objects, properties and categories can be described so that software agents can interpret them. The set of objects can be information on a mechanical axis of a leg, a mechanical axis of a femur, a mechanical axis of a tibia, a rotation axis of a femur, a rotation axis of the tibia, an anatomic axis of the femur, an anatomic axis of the tibia, a biomechanical axis of the patella, a rotation axis of the patella, an anatomic axis of the patella, a transepicondylar line, a Whiteside's line, a medial joint line, a lateral joint line, a tibial slope, a tibial offset, a tibial plateau dimension, a tibial plateau perimeter, a dimension, a perimeter, a surface, a volume of a cut tibial plateau, a femoral offset, a femoral condyle, trochlea, distal femur dimension, a femoral perimeter, e.g. a perimeter of a femoral condyle, a dimension, a perimeter, a surface, a volume of a cut distal femur, e.g. a cut femoral condyle or a trochlea; any of the foregoing structures or combinations thereof and/or parameters can be used in any of the embodiments described in the specification. The set of objects can be used by the computer system and, optionally, at least one artificial neural network (ANN) for aligning the virtual implant component, e.g. in relationship to one or more of a mechanical axis of a leg, a mechanical axis of a femur, a mechanical axis of a tibia, a rotation axis of a femur, a rotation axis of the tibia, an anatomic axis of the femur, an anatomic axis of the tibia, a biomechanical axis of the patella, a rotation axis of the patella, an anatomic axis of the patella, a transepicondylar line, a Whiteside's line, a medial joint line, a lateral joint line, a tibial slope, a tibial offset, a tibial plateau dimension, a tibial plateau perimeter, a dimension, a perimeter, a surface, a volume of a cut tibial plateau, a femoral offset, a femoral condyle, trochlea, distal femur dimension, a femoral perimeter, e.g. a perimeter of a femoral condyle, a dimension, a perimeter, a surface, a volume of a cut distal femur, e.g. a cut femoral condyle or a trochlea, or combinations thereof. The aligning can be automatic, e.g. by the computer system and/or the ANN, semi-automatic or manual, e.g. by the surgeon using a graphical user interface controlled by at least one computer processor.

The semantics of these can be captured as description logic concepts, roles and individuals and can be implemented as classes, classifications and/or properties. These can also be described as ontologies, e.g. a set of concepts and categories in a subject area or domain that shows their properties and the relations between them. The most general ontologies can be identified as upper ontologies which can act as mediators between domain ontology. Upper ontologies can, for example, involve concepts and/or categories related to pre-operative, intra-operative and/or postoperative patient management. Domain ontologies can, for example, involve concepts and/or categories related to intra-operative anesthesia management or intra-operative nursing care or intra-operative imaging and imaging studies. Knowledge representations of this kind can be suitable for content-based indexing and retrieval, scene interpretation, and clinical decision support. Knowledge representation of this kind can be used for knowledge discovery via automated reasoning, e.g. by inferring new statements based on explicitly stated ore recognized knowledge. Video data and events can be represented as sematic web rule language (SWRL) which can, for example, be used to express rules and/or logic combining, web ontology language with rule mark up language.

Artificial intelligence systems, techniques and/or methods (AI) can assess data and can be used to select an implant component with the fit and/or size and/or shape optimized for a particular patient. AI make predictions, including, for example, therapeutic recommendations or modifications, based on data obtained in the environment. AI can also evaluate the predictions and adapts based on its assessment. AI can predict postoperative outcomes based on a selected implant fit, size, and/or shape.

According to various embodiments, a system to determine a treatment plan for a patient undergoing treatment is provided comprising at least one computer system comprising at least one processor, wherein the at least one processor is configured to receive preoperative, intraoperative or preoperative and intraoperative data about the patient undergoing treatment from one or more data sources, wherein the preoperative, intraoperative or preoperative and intraoperative data can be imaging data, e.g. from a CT scan, MRI scan, ultrasound data, data generated based on one, two or more x-rays, wherein the at least one processor is configured to compare at least one size, fit or shape of a virtual implant component, with the preoperative, intraoperative or preoperative and intraoperative data, and wherein the at least one processor is configured to select at least one size, fit or shape of a virtual implant component based on the size, fit or shape of the virtual implant component and based on the preoperative, intraoperative or preoperative and intraoperative data.

In some embodiments, the at least one computer system comprises at least one processor, wherein the at least one processor is configured to receive preoperative, intraoperative or preoperative and intraoperative data about the patient undergoing treatment from one or more data sources, wherein the preoperative, intraoperative or preoperative and intraoperative data can be imaging data, e.g. from a CT scan, MRI scan, ultrasound data, data generated based on one, two or more x-rays, wherein the at least one processor is configured to compare at least one size, fit or shape of a virtual implant component, with the preoperative, intraoperative or preoperative and intraoperative data, and wherein the at least one processor is configured to recommend at least one size, fit or shape of a virtual implant component based on the size, fit or shape of the virtual implant component and based on the preoperative, intraoperative or preoperative and intraoperative data.

In some embodiments, the recommending and/or selecting of at least one of a size, fit, or shape (or combination thereof) of a virtual implant can be performed using a single parameter. In some embodiments, the recommending and/or selecting of at least one of a size, fit, or shape (or combination thereof) of a virtual implant can be performed using multiple parameters. The one or more parameters can be, for example, a fit in relationship to, a size in relationship to, a shape in relationship to, an alignment in relationship to at least one of an anatomic structure, an anatomic landmark, a mechanical axis of a leg, a mechanical axis of a femur, a mechanical axis of a tibia, a rotation axis of a femur, a rotation axis of the tibia, an anatomic axis of the femur, an anatomic axis of the tibia, a biomechanical axis of the patella, a rotation axis of the patella, an anatomic axis of the patella, an abduction axis or line, e.g. on the contact surface of two opposing articular surfaces, an adduction axis or line, e.g. on the contact surface of two opposing articular surfaces, a transepicondylar line, a Whiteside's line, a femoral, tibial, patellar contact surface or combinations thereof, a femoral, tibial, patellar contact line, or combinations thereof, a medial joint line, a lateral joint line, a tibial slope, a tibial offset, a tibial plateau dimension, a tibial plateau perimeter, a dimension, a perimeter, a surface, a volume of a cut tibial plateau, an anterior margin of a tibial plateau (before and/or after a bone removal, e.g. a bone cut or a burring), a posterior margin of a tibial plateau (before and/or after a bone removal, e.g. a bone cut or a burring), a medial margin of a tibial plateau (before and/or after a bone removal, e.g. a bone cut or a burring), a lateral margin of a tibial plateau (before and/or after a bone removal, e.g. a bone cut or a burring), a femoral condyle offset, a femoral condyle, a trochlea, a distal femoral dimension, a posterior femoral dimension, a femoral perimeter, e.g. a perimeter of a femoral condyle, a dimension, a perimeter, a surface, a volume of a cut distal femur, e.g. a cut femoral condyle or a trochlea, a medial, inferior, lateral, superior, anterior, posterior margin of a cut distal femur, e.g. a posterior femoral condyle, a dimension, an anterior femoral cortex, e.g. to avoid notching of a femoral component, a perimeter, a surface, a volume of an uncut or a cut or milled patella, a shape of a medial patellar facet, a shape of a lateral patellar facet, a shape of a patella, a trochlear sulcus, a trochlear sulcus line, a depth of a trochlear sulcus, a trochlear height, e.g. for assessing the fit, size, and/or shape of an anterior flange of a femoral component, a radius, a curvature, a shape of an articular surface, e.g. a femoral condyle, a tibial plateau, a patella, at least a portion of an internal or external margin, periphery, edge, perimeter, anteroposterior, mediolateral, oblique dimension, diameter, radius, curvature, geometry, shape or surface of one or more structures of a physical joint, e.g. a cortical bone, subchondral bone, cartilage, damaged or diseased cartilage, or combination thereof.

Knee:

The one or more parameters can be, for example, at least one of a coordinate, a peripheral margin, a dimension, a shape, a radius, a convexity, a concavity of at least one of a medial wall of the femoral notch, a lateral wall of the femoral notch; a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau surface, a lateral tibial plateau surface, a medial tibial plateau surface, a lateral tibial plateau surface, any of the foregoing tissues and/or structures on a surgically exposed surface, any of the foregoing tissues and/or structures in a subsurface location or combinations thereof.

Anatomic structures or anatomic landmarks in a hip and shoulder joint can comprise one or more of the following listing.

Hip:

The one or more parameters/anatomic structures can be at least one of a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a fovea capitis, a transverse acetabular ligament, a pulvinar, a ligamentum teres, a labrum, one or more osteophytes, femoral and/or acetabular or any combinations of the foregoing.

Shoulder:

The one or more parameters/anatomic structures can be at least one of a portion or an entire glenoid, a portion or an entire coracoid process, a portion or an entire acromion, a portion of a clavicle, a portion or an entire humeral head, a portion or an entire humeral neck, a portion of a humeral shaft, one or more humeral osteophytes, one or more glenoid osteophytes, a portion or an entire glenoid labrum, a portion or an entire shoulder ligament, e.g. a coracoacromial ligament, a superior, middle, or inferior glenohumeral ligament, a portion of a shoulder capsule or any combinations of any of the foregoing.

The foregoing anatomic landmarks, surfaces and features are only exemplary and are not meant to be limiting. Someone skilled in the art can readily identify other anatomic landmarks, surfaces, geometries, shapes or features that can be used for purposes of registration of virtual data and live data of the patient or other data of the patient and/or surgical instruments. Any of the anatomic landmarks and/or anatomic structures listed in the foregoing sections can be used for any of the other embodiments throughout the specification.

In some embodiments, the at least one computer system is configured to generate the treatment plan using an implant recommended or selected using an artificial neural network. In some embodiments, the artificial neural network is a generative neural network. In some embodiments, the artificial neural network includes a training configuration. In some embodiments, the training configuration of the artificial neural network is based on a training data set comprising one or more of preoperative data, intraoperative data and postoperative data from one or more existing patients. In some embodiments, the training configuration is configured to be updated with postoperative data from the patient undergoing treatment. Postoperative data can include patient reported outcome scores, objective outcome measurements, physician assessment, clinical examination, functional outcome measurements etc.

In some embodiments, the preoperative data includes one or more of CT images, MR images, x-ray images, ultrasound images, PET images, SPECT images, nuclear scintigraphy images, thermography images, wearable devices data, IMU data, patient history, ECG data, clinical assessments, patient reported outcome measurements, range of motion measurements, clinical and function scores, objective and subjective outcome measurements.

In some embodiments, the postoperative data includes one or more of CT images, MR images, x-ray images, ultrasound images, PET images, wearable devices data, IMU data, patient history, ECG data, clinical assessments, patient reported outcome measurements, range of motion measurements, clinical and function scores, objective and subjective outcome measurements, economic outcomes.

In some embodiments, the treatment plan comprises one or more of a surgical plan, surgical procedure step, resection plane, drill path, implant, implant fit, implant size, implant shape, implant position, implant rotation, anatomical models, distance measurement, angle measurement, axis and instruction.

In some embodiments, the at least one computer system is configured to recommend or select the implant fit, size and/or shape using an artificial neural network. In some embodiments, the artificial neural network is a discriminative neural network. In some embodiments, the artificial neural network includes a training configuration. In some embodiments, the training configuration of the artificial neural network is based on a training data set comprising one or more of preoperative data, intraoperative data and postoperative data from one or more existing patients. In some embodiments, the training configuration is configured to be updated with postoperative data from the patient undergoing treatment. In some embodiments, the preoperative data includes one or more of CT images, MR images, x-ray images, ultrasound images, PET images, SPECT images, nuclear scintigraphy images, thermography images, wearable devices data, IMU data, patient history, ECG data, clinical assessments, patient reported outcome measurements, range of motion measurements, clinical and function scores, objective and subjective outcome measurements.

In some embodiments, the postoperative data includes one or more of CT images, MR images, x-ray images, ultrasound images, PET images, SPECT images, nuclear scintigraphy images, thermography images, wearable devices data, IMU data, patient history, ECG data, clinical assessments, range of motion measurements, clinical and function scores, objective and subjective outcome measurements, economic outcomes.

In some embodiments, the recommending or selecting an implant, e.g. based on at least one of fit, size and/or shape, comprises one or more of a surgical plan, surgical procedure step, resection plane, drill path, implant, implant size, implant position, implant rotation, anatomical models, distance measurement, angle measurement, axis and instruction.

Artificial Neural Networks

AI can utilize, for example, neural networks. Artificial neural networks (ANNs) can learn tasks based on examples, e.g. without task specific programming. ANNs can be based on a group of connected units or nodes, i.e. artificial neurons. Each connection between artificial neurons can generate a signal to be transmitted to another artificial neuron. One or more artificial neurons can receive the signal and process it and, for example, use it to initiate a task. The signal at a connection between artificial neurons can be a number, and the outputs can be calculated by various functions or algorithms, e.g. non-linear functions. Artificial neurons can have a weight assigned to them, which can amplify or de-emphasize their signal. Artificial neurons can be organized in layers, with different layers performing different kind of transformations. Artificial neural networks can utilize various techniques, processes and/or algorithms, e.g. backpropagation, parallel distributed processing, max-pooling, Hebbian learning, long term potentiation, support vector machines, and linear classifiers. ANNs can include recurrent neural networks and deep feedforward neural networks. ANNs can perform functions such as, for example, pattern recognition and machine learning. Components of ANNs can include neurons, connections and weights, propagation functions, and learning rules. Neurons can include an activation component, a threshold component, an activation function, and an output function. ANNs can define mathematical and other functions. ANNs can use predefined functions, e.g. hyperbolic tangent function, sigmoid function, softmax function or rectifier function.

ANNs can be used for learning. Learning can comprise using a number of observations to find a function which solves a predetermined or desired task in an optimal sense, e.g. an optimal outcome. Learning can be supervised learning, unsupervised learning and reinforcement learning. Supervised learning can use one or more sets of example pairs and the goal can be, for example, to find a function in an allowed class of functions that matches the examples. Pattern recognition, classification, and regression can be part of supervised learning. Supervised learning can use informational fuzzy networks, random forests, nearest neighbor algorithms, logistic model tree, and other algorithms. Supervised learning can use statistical classification, including, for example, decision trees, Bayesian networks, and/or linear classifiers.

In unsupervised learning, a set of data can be provided for example along with a cost function to be minimized, which can be a function of the data and the network output. The cost function can be dependent on the task and the properties of the parameters and observed variables or data. Unsupervised learning can be applied, for example, to pattern recognition, classification, and regression, general estimation problems, clustering, the estimation of statistical distributions, compression and filtering. Unsupervised learning can use one or more ANNs, expectation-maximization algorithms, data clustering, and the like. Association rule learning can use a priori algorithms, eclat algorithms, FP-growth algorithms, hierarchical clustering (e.g., single-linkage clustering and conceptual clustering), partitional clustering (e.g., K-means algorithm, fuzzy clustering), reinforcement learning (e.g., Monte Carlo method, Q-learning, temporal difference learning, and combinations thereof.

In reinforcement learning, data can be generated by an agent's interactions with one or more objects, e.g. a surgeon interacting with a patient. The agent, e.g. the surgeon, can perform an action, and the environment, e.g. a target tissue or a surgical site, can generate one or more observations and, for example, a cost according to some dynamics or parameters, e.g. a tissue removal or an infection risk. The objective can be to discover a treatment, treatment algorithm, treatment modification that can reduce or minimize a measure of the cost, e.g. an infection risk, a patient reported outcome measurement, a functional result. The parameters and dynamics of the environment, e.g. a surgical site, can be unknown, but can be estimated. The environment, e.g. a target tissue or a surgical site, can be modeled as a Markov decision process and actions, with possible probability distributions, e.g. a cost distribution, an observation distribution, and one or more transitions, and a policy or algorithm or solution can be defined as a conditional distribution over actions given one or more observations. Dynamic programming can be coupled with ANNs and applied to multi-dimensional nonlinear problems.

Learning can utilize one or more cost functions, e.g. the cost being an excellent or a poor clinical outcome. The cost function can yield information of how far a particular solution, e.g. a clinical treatment, treatment sequence or treatment algorithm or surgical technique, is from an optimal outcome, e.g. an excellent score in a patient reported outcome measure. ANNs can find the solution, e.g. a clinical treatment, treatment sequence or treatment algorithm or surgical technique, that yields the lowest cost, e.g. distance or amount away from an optimal outcome or excellent score in a patient reported outcome. The cost can be a function of the observations. The cost can be described as a statistic. A cost can be the mean squared error, which can try to minimize the average squared error between the network's output and one or more target values over example pair(s). A cost function can be selected or predetermined for a particular problem set, e.g. a clinical problem set or clinical observation data, e.g. pre-operative, intra-operative or post-operative data. AI can find and develop one or more optimal cost functions for a set of observational data and AI can refine the cost function as the size of the observational data set increases.

Machine Learning

Machine learning can comprise supervised learning, semi-supervised learning, active learning, reinforcement learning or unsupervised learning. With supervised learning, the computer can receive example inputs and desired outputs, which can be provided from a database or using a learning tool; the objective is to learn one or more rules that map the inputs to the outputs. Semi-supervised learning can be different in that the computer can be given an incomplete training example input, optionally with some desired outputs missing. With active learning, the computer can only obtain training inputs for a limited set of examples, and the computer can optimize the choice of inputs to acquire labels for. With reinforcement learning, training data, e.g. inputs and desired outputs can be given only as feedback to the program's actions in a dynamic environment, such as guiding a surgery. With unsupervised learning, no training input and/or output data are provided, leaving the computer and computer processor on its own to find structure in the inputs.

Machine learning can use processes such as, for example, classification, regression, clustering, density estimation, dimensionality reduction, and topic modeling. With classification, inputs can be divided into two or more classes, and, for example, the learning system can produce a model that assigns unseen inputs to one or more of these classes. Data can be classified, for example, into "excellent", "good", "acceptable" or "poor" outcome, e.g. clinical outcome. Numeric values or ranges of numeric values can be assigned to different classes, for example numeric values or ranges of numeric values from a patient reported outcome measurement, from a clinical reporting system, and/or from one or more electronic measurements. With regression, outputs can be continuous rather than discrete. Regression can be used, for example, when patient outcomes are continuous. With clustering, inputs can be divided into groups. The groups cannot be known beforehand; thus, with clustering learning can be unsupervised. With density estimation, the distribution of inputs in a given space or sample can be determined. With dimensionality reduction, inputs can be simplified by mapping them into a lower-dimensional space. With topic modeling, a machine learning system can be given a list of human language documents and can be tasked to find out which documents cover similar topics.

Developmental learning can include robotic learning, which can generate its own learning situations to acquire new skills through autonomous self-exploration and interaction, for example, with human teachers.

A goal of machine learning or deep learning can be to generalize from the experience. Generalization can be the ability of a learning machine or system to perform accurately on new, unseen inputs after having been trained on a training data set. Training examples can come from an unknown probability distribution and the learning machine or system can be tasked to build an input and output model that enables it to produce sufficiently accurate predictions with new inputs. Bounds or limits, e.g. probabilitistic bounds, on the performance, accuracy and reproducibility of machine learning can be determined. When machine learning is used for solving clinical problems, e.g. outcome prediction or treatment planning or modification, the bounds or limits of performance, accuracy and/or reproducibility of the machine learning system or learning machine can influence and/or determine the performance accuracy, and/or reproducibility of the clinical application, e.g. outcome prediction or treatment planning or modification. Accuracy can include the assessment of true positives, true negatives, false positives and false negatives. Reproducibility can be precision. Performance of the machine learning system and/or learning machine can include other statistical measures known in the art for assessing the performance of a clinical system.

Learning systems including machine learning can use decision tree learning, association rule learning, artificial neural networks (ANNs), deep learning, inductive logic programming, support vector machines, clustering, Bayesian networks, reinforcement learning, representation learning, similarity and metric learning, sparse dictionary learning biologic or genetic algorithms, rule based machine learning and learning classifier systems.

With decision tree learning, a decision tree can be used as a predictive model, which can map observations about one or more parameters to conclusions about the parameter's target value. With association learning, relations between variables or parameters can be identified in large databases. With ANNs, computations can be structured through an interconnected group of artificial neurons, processing information using a connected approach. ANNs can be non-linear data modeling tools, using various statistical methods and approaches known in the art. Deep learning can employ multiple layers in an artificial neural network. Inductive logic programming (ILP) can utilize logic programming for rule learning, e.g. using a uniform representation for input examples, background knowledge, and hypotheses. Support vector machines (SVMs) can be a set of supervised learning methods used for classification and/or regression. A given a set of training examples can be marked as belonging to first category or a second category; an SVM training machine can build a model predicting whether a new input falls into the first or the second category.

Clustering can be the assignment of a set of observations into subsets, where data in each subset have similarities with regard to one or more parameters while data in different subsets can be dissimilar with regard to one or more parameters. Clustering techniques can provide information on similarity or dissimilarity, for example reflected in a similarity metric, a measurement of internal compactness or separation between different clusters. A Bayesian network can be a graphical model representing, for example, random variables and their conditional independencies. This can be shown in a directed acyclic graph. A Bayesian network can represent the probabilistic relationships between diseases and symptoms. A Bayesian network can be used to compute the probability(ies) of the presence of one or more disease.

With reinforcement learning, input and output pairs can never be presented; reinforcement learning can map a state, e.g. a clinical state of a patient, and can develop predictions, actions or treatment the system can make. With representation learning algorithms input information can be preserved but transformed to make it more useful, e.g. as a pre-processing step, prior to performing classification or predictions, allowing reconstruction of the inputs coming from the unknown data generating distribution.

Deep learning can utilize multiple levels of representation, e.g. in an ANN. Higher-level, e.g. more abstract, parameters or data can be defined as generating lower-level parameters or data. With similarity learning, the learning system or machine can be given pairs of data that are considered similar and pairs of less similar data. It can then learn a similarity function or a distance metric function that can predict if new objects are similar.

Rule-based machine can be identification and utilization of a set of relational rules that can represent the knowledge captured by the learning system. Learning classifier systems (LCS) can be a family of rule based machine learning algorithms or systems which can combine a discovery component with a learning component.

The accuracy of classification machine learning models can be evaluated using accuracy estimation techniques and statistical techniques and methods testing the accuracy, sensitivity, specificity, fake positive and false negative rates. Other statistical methods such as Receiver Operating Characteristic (ROC) and associated Area under the Curve (AUC) as well as Total Operating Characteristic (TOC) can be used.

Deep Learning

Deep learning can include machine learning algorithms which can use multiple layers of non-linear processing units or elements. Each layer can use the output from a higher layer as input. Deep learning systems can work in a supervised setting, e.g. using one more classification systems. Deep learning systems can also work in an unsupervised setting, e.g. in the context of texture analysis or pattern recognition. Deep learning systems can learn multiple levels of representations that correspond to different levels of abstraction. The different levels can form an order or a hierarchy of concepts. The different layers of a deep learning system can reside in different layers of an artificial neural network, i.e. a deep neural network. They can include hidden layers in an ANN. Deep learning systems and deep ANNs can utilize Boltzmann machines. With deep learning systems, layers can correspond to layers of abstraction, e.g. across a deep neural network. Varying numbers of layers and layer sizes can provide different degrees of abstraction. Higher level, more complex concepts can be learned from lower level layers.

Deep neural networks (DNNs) can be one or more ANNs with multiple hidden layers between the input and output layers. DNNs can model complex non-linear relationships. DNNs can generate models where the object is expressed as a layered composition. DNNs can be feedforward networks in which data flows from the input layer to the output layer without looping back. DNNs can be recurrent neural networks or convolutional deep neural networks.

Deep learning algorithms can be applied to unsupervised learning tasks. This is an important benefit because unlabeled data can more abundant than labeled data. For example, in a clinical environment, a deep learning system with a multi-layered ANN can initially be trained using a classification of outcomes in a supervised fashion. As the data grow, the system can optionally learn in an unsupervised manner, for example by utilizing pattern recognition across large clinical datasets, which can include pre-operative intra-operative and post-operative data.

Classification

Classification can be a process of creating categories, in which data or objects can be recognized, differentiated or understood. A classification system can be an approach of accomplishing classification. Classification can be performed using mathematical classification, statistical classification, classification theorems, e.g. in mathematics, and attribute value systems. Classifications can be alphanumeric. Classifications can be single or multi-dimensional. Classifications can be single or multi-layered. Classifications can be color coded. An ANN can use a single classification system, e.g. in supervised learning. An ANN can use multiple classification systems. When multiple classification systems are used, they can reside in different layers of a DNN or deep learning system.

Classification can be the problem of identifying to which of a set of categories or sub-populations a new observation belongs; this can be determined, for example, using a training data set with observations whose category membership is known. For example, a diagnosis can be assigned to a patient as a category which can be described by measured data or characteristics such a heart rate, blood pressure, presence of absence of symptoms or combinations of symptoms. Classification can be a pattern recognition.

Individual observations or data can be divided into a set of quantifiable properties. These properties may be categorical, e.g. "a", "b", "c", "d" etc. or ordinal, e.g. "excellent", "very good", "good", "acceptable", "average", or "poor". They can be integer or real valued. Observations or data can also be classified using similarity or distance functions, e.g. based on earlier observations or data. An algorithm that implements classification can be a classifier. A classifier can sometimes also be a mathematical function, e.g. implemented by a classification algorithm, that can map input data to a category.

Data can be classified, for example, into "excellent", "good", "acceptable" or "poor" outcome, e.g. one or more clinical outcomes or clinical outcome variables. Numeric values or ranges of numeric values can be assigned to different classes, for example numeric values or ranges of numeric values from a patient reported outcome measurement, from a clinical reporting system, and/or from one or more electronic measurements.

Discriminative Vs. Generative Models and Networks

In machine learning, discriminative models can be distinguished from generative models.

1. Discriminative models are trained to learn the boundaries between classes. They model the conditional probability of a target variable Y (class), given an observation x: $P(Y|X=x)$ ("probability of Y given X=x"). Discriminative models describe the probability for classifying a given example x into a classy E Y. Discriminative models include, for example, logistic regression, conditional random fields, support vector machines, neural networks, random forests, or perceptrons.

Generative models model the distribution of individual classes. They can generate data and provide a statistical model of the joint probability distribution on X×Y, $P(X,Y)=P(X|Y)*P(Y)$, for an observable variable X and a target variable Y. Generative models include, for example, naïve Bayes models and Bayes networks, hidden Markov models, Boltzmann machines, variational autoencoders or generative adversarial networks (GAN).

In some embodiments, the computer system can use a trained artificial neural network (ANN) to determine the treatment plan. The ANN can implement a discriminative model. A discriminative model can be trained to classify the input data, i.e. the preoperative and/or intraoperative data and/or postoperative data, into different classes, wherein each class can represent a different treatment plan.

In some embodiments, the ANN can implement a generative model. Instead of assigning preoperative and/or intraoperative input data and/or postoperative data to an existing class, a generative model is trained to generate the treatment plan steps based on the input data.

In some embodiments, a generative and a discriminative network model can be combined into a generative adversarial network (GAN) to generate a treatment plan. Using a training data set of existing recorded treatment plans for a number of preoperative and/or intraoperative input data and/or postoperative data sets, in this situation, the generative network can be trained to generate a preferred treatment plan from the preoperative and/or intraoperative input data. The discriminative network can be trained to evaluate the generated treatment plan and to distinguish the generated treatment plan from the actual treatment plan of the training case. Thus, the discriminative network can force the generative network to improve its results.

Mechanical Axis Alignment

In some embodiments, the mechanical axes of the knee joint can be determined. The mechanical axis of the leg can be the axis extending from the center of the hip joint, e.g. the center of rotation of the hip, to the center of the ankle joint.

In some embodiments, the mechanical axis of a bone can also be determined. For example, the mechanical axis of the femur can be determined. The mechanical axis of the femur can, for example, be determined as the axis connecting the center of the hip joint and the center of the distal femur. The mechanical axis of the tibia can, for example, be determined as the axis connecting the center of the proximal tibia and the center of the ankle joint.

The mechanical axis of the leg can be determined using am imaging test, e.g. full leg x-rays (e.g. standing, weight-bearing or lying down), a CT scan with either a scout scan through the hip and ankle (and, for example, CT slices or a 3D volume or spiral through the knee joint) or CR slices or 3D volume or spiral through the hip joint and/or the ankle joint and, optionally, the knee joint, an MRI scan with select sequences through the hip and/or ankle joint and, optionally the knee joint. Imaging studies can include multi-planar x-rays, for example as obtained using an EOS system (EOS, Paris, France).

In some embodiments, the mechanical axis can be determined using surgical navigation, e.g. using RF or navigation markers, IMU's and/or optical markers.

A computer processor can then, for example, orient and/or align one or more virtual implant components to be aligned with a desired or predetermined mechanical axis correction, which can be a mechanical axis correction to neutral mechanical axis, a mechanical axis correction to anatomic alignment, and/or an partial mechanical axis correction, e.g. to retain some residual varus or valgus deformity of the patient, e.g. 1 degree, 2 degrees, 3 degrees, 0.5 degrees or any other value.

A computer processor can then, for example, orient and/or align one or more virtual implant components to be aligned with a predetermined or desired mechanical axis alignment of the joint and/or the implant component. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is aligned with the predetermined or desired mechanical axis, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the mechanical axis alignment of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the mechanical axis alignment of the one or more implant components in order to find a compromise between mechanical axis alignment and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Rotation, Rotation Axes

The location, orientation, alignment, speed, trajectory and changes thereof of IMU's and/or navigation markers and/or image capture markers, e.g. optical markers with geometric patterns and/or LED's, including combinations thereof can yield information on knee kinematics and/or shape and morphology of the joint, e.g. a knee joint, shoulder joint, ankle joint, hip joint, including one or more rotation axes of a joint.

The location, orientation, alignment, speed, trajectory and changes thereof of the IMU's and/or navigation markers and/or image capture markers, e.g. optical markers with geometric patterns and/or LED's, including combinations thereof can also yield information on the center of rotation or flexion and extension or abduction and adduction of a joint for certain exercises or activities or the center of rotation or flexion and extension or abduction and adduction of the knee for certain exercises or activities, e.g. tibiofemoral rotation or patellofemoral rotation. This information can be used to determine one or more rotation axes, for example around the knee, hip or ankle, which can optionally be used to determine any rotational deformity if applicable and any desired rotational correction, if applicable, and which can be used in a virtual surgical plan or with a process to evaluate the fit of one or more implant components, for example with select partial or complete rotational deformity correction, for example for a given rotational alignment of the one or more implant components. In another embodiment, the determination of the one or more rotation axes, e.g. around the knee, e.g. a tibiofemoral rotation axis or a patellofemoral rotation axis can be used with the aim of placing one or more implant components so that the one or more articulating surfaces substantially or, at least in part, restore the rotation axes of the patient for a given implant system, e.g. a femoral component and a tibial component or a femoral component and a patella femoral component, e.g. also by aligning one or more articular surfaces of an implant component with one or more articular surface(s) of the patient.

In some embodiments, the rotation axis or axes of a joint can be estimated using, for example, n imaging test. For example, the tibial tuberosity can be used for determining a predetermined or desired tibial component alignment and/or tibial component rotation axes. The femoral transepicondylar axis or posterior femoral axes or other axes or biomechanical estimates (e.g. by placing one or more cylinders virtually inside the posterior medial and lateral condyles to determine or derive their respective rotation axes) can also be estimated using information derived from one or more imaging tests.

A computer processor can then, for example, orient and/or align one or more virtual implant components to be aligned with a predetermined or desired rotation axis of the joint and/or the implant component. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is aligned with one or more rotation axes of the joint, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the rotational alignment of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the rotational alignment of the one or more implant components in order to find a compromise between rotational alignment and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Tibial Slope

In some embodiments, a tibial slope can be determined. The tibial slope can be a medial tibial slope. The tibial slope can be a lateral tibial slope. The medial tibial slope can be measured, for example, by connecting the highest point on the anterior medial tibia with the highest point on the posterior medial tibia as seen, for example, on a lateral radiograph or a 2D or 3D scan, e.g. an ultrasound, a CT or MRI scan. The lateral tibial slope can be measured, for example, by connecting the highest point on the anterior lateral tibia with the highest point on the posterior lateral tibia as seen, for example, on a lateral radiograph or a 2D or 3D scan, e.g. an ultrasound, a CT or MRI scan. Radiographs can be obtained in supine or upright, standing position.

A tibial slope can be measured for the anterior tibia and the posterior tibia. For example, an anterior medial tibial slope can be measured by connecting the highest point on the anterior medial tibia with the lowest point in the medial tibial plateau. A posterior medial tibial slope can be measured by connecting the lowest point in the medial tibial plateau with the highest point on the posterior medial tibia. An anterior lateral tibial slope can be measured by connecting the highest point on the anterior lateral tibia with the lowest point in the lateral tibial plateau. A posterior lateral tibial slope can be measured by connecting the lowest point in the lateral tibial plateau with the highest point on the posterior lateral tibia. The tibial slope can be determined, for example, by measuring the angle between any of the resultant lines and the perpendicular line to the ground or, for example, by measuring the angle between any of the resultant lines and one or more tibial axes, e.g. the long axis of the tibia. Optionally, the distance from the anterior medial cortex or the posterior medial cortex to lowest point on the medial tibial plateau can be determined. Optionally, the distance from the anterior lateral cortex or the posterior lateral cortex to lowest point on the lateral tibial plateau can be determined.

The one or more measurement(s) of one or more tibial slopes can optionally be introduced into a virtual surgical plan, for example as displayed by a computer monitor during surgery or during the sizing and fitting and determination of implant overhang or undersizing. The virtual surgical plan can entail that the same one or more tibial slopes, e.g. a medial slope and/or a lateral slope, or an average of the two or other combinations of the two be preserved after placement of the one or more virtual implant components in the virtual surgical plan, e.g. as displayed by a computer monitor, and, ultimately, after placement of the actual one or more implant components during the live surgery. Alternatively, a medial slope, a lateral slope, an average of the two or other combinations of the two can be corrected. For example, they can be set to a fixed medial slope, a fixed lateral slope, a fixed average of the two or a fixed other combination of the two. For example, a 5 degree fixed slope medially and laterally can be chosen in a virtual surgical plan. Or a 3 degree fixed slope medially or laterally can be chosen in a virtual surgical plan. Or a 2 degree fixed slope medially or laterally can be chosen in a virtual surgical plan. Or a 0 degree fixed slope medially or laterally can be chosen in a virtual surgical plan.

With some posterior stabilized implants, a 0 degree fixed slope can be chosen, although other fixed slopes such as 2, 3, and 5 degrees or any other value are possible. With some posterior cruciate retaining implants, a 5 degree fixed slope can be chosen, although other slopes such 0 degrees, 2 degrees or 4 degrees or any other value are possible.

The fitting and/or sizing and/or determination of implant overhang, implant undersizing and/or implant bone coverage can be determined for one or more tibial slopes.

In some embodiments, at least one slope that is similar to or identical to the native slope of the unoperated patient can be used. For example, in some embodiments, the patient's medial slope and/or the patient's lateral slope can be preserved. In some embodiments, the patient's native medial slope can be preserved in the virtual surgical plan, while the lateral slope may not be preserved. For example, the lateral slope may be fixed or may be set equal to the patient's medial slope or at a value or ratio between the two. In some embodiments, the patient's native lateral slope can be preserved in the virtual surgical plan, while the medial slope may not be preserved. For example, the medial slope can be fixed or may be set equal to the patient's lateral slope or at a value or ratio between the two.

Replicating the patient's native medial tibial slope and lateral tibial slope can be achieved in the virtual surgical plan and during the actual surgery by choosing separate medial and lateral tibial plateau components which can then be placed with different slopes relative to each other by placing the virtual tibial cuts and, in the live patient, the actual tibial cuts at an angle close to or substantially similar to the patient's native medial and lateral slopes. If a mono-component tibial tray or polyethylene is used for a total knee replacement to cover the entire tibial plateau, the tibia can be cut at a single angle or slope in the virtual surgical plan and during the actual surgery in the live patient. In this instance, the patient's native medial and/or lateral tibial slope can be maintained with use of a polyethylene component that has different medial and lateral slopes integrated into the medial and lateral polyethylene shape. For example, the medial and lateral polyethylene shape used in the virtual surgical plan, for example as displayed by a computer monitor, and during the actual surgery in the live patient can closely resemble the medial and lateral slope and, optionally, shape of the patient's native tibia. Optionally, the polyethylene can only resemble the native anterior and/or the native posterior slope of the patient's medial and/or lateral tibial plateau. In some embodiments, insert components or polyethylene components can be selected that closely match the native medial and/or lateral slope(s) of the patient, for a virtual cut of the patient's tibia. The virtual cut can be selected or adjusted in the virtual surgical plan to maximize the match between the patient's native medial and lateral slopes and the medial and lateral slope of the polyethylene and/or inserts. The virtual cut can be adjusted and with it the slope can be adjusted to optimize the amount of bone coverage by the implant component. Any adjusting can be manual, e.g. using a user interface driven by a computer processor, semi-automatic, or automatic, e.g. using one or more computer processors.

In some embodiments, the computer monitor can display the patient's medial and/or lateral slope, for example through a colored or dotted line. The computer monitor can also display the intended medial and/or lateral slope, for example as defined in a virtual surgical plan. The intended medial and/or lateral slope can be displayed with a colored or dotted line or plane, optionally different from the patient's native slope(s) if they are also being displayed. The surgeon can then direct a bone saw or burr or other surgical instrument so that the bone saw, burr or other surgical instrument will substantially execute a removal of portions of the proximal tibial plateau to achieve placement of the implant with the one or more of the intended medial and/or lateral slopes. Optionally, the anterior slope of the medial and/or lateral polyethylene can be steeper than the patient's native anterior medial or anterior lateral slope. Optionally, the posterior slope of the medial and/or lateral polyethylene can be steeper than the patient's native posterior medial or anterior lateral slope. Optionally, the anterior slope of the medial and/or lateral polyethylene can be less steep than the patient's native anterior medial or anterior lateral slope. Optionally, the posterior slope of the medial and/or lateral polyethylene can be less steep than the patient's native posterior medial or anterior lateral slope. Any fitting, sizing, placing, aligning and/or selecting of one or more virtual and, in the live patient, also physical implant components can take these differences into account.

In some embodiments, measurements of one or more tibial slopes can be obtained with the patient in supine position. Alternatively, measurements of the patient's tibial slope can be obtained with the patient in prone position. Alternatively, measurements of the patient's tibial slope can be obtained in upright position. In some embodiments, the imaging data, e.g. x-ray, ultrasound, CT scan or MRI, can be obtained with use of a positioning device or a leg holder. Typically, the positioning device or leg holder can be used to control the degree of knee flexion or extension (see, for example, the Synaflex knee positioning device by Synarc, Inc.). The positioning device or leg holder can be used to control the degree of knee rotation or leg rotation. In an embodiment, x-ray, ultrasound, CT and/or MRI scans are obtained with the leg in zero rotation or, alternatively, a defined degree of internal or external rotation, e.g. 5 degrees of internal or external rotation. In some embodiments, the same or a similar positioning device or leg holder can be used during the surgery, preferably utilizing the same degrees of flexion or extension and/or rotation as was used during any of the pre-operative imaging studies.

A computer processor can then, for example, orient and/or align one or more virtual implant components to be aligned with a predetermined or desired tibial slope of the joint and/or the implant component. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is aligned with the tibial slope, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the alignment relative to the slope of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Optionally, the operator or computer processor can modify the alignment relative to the slope of the one or more implant components in order to find a compromise between alignment relative to the slope and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Femoral Offset

In some embodiments, a computer processor can determine or can be used to determine and/or display the patient's femoral offset, e.g. a medial distal femoral offset; a lateral distal femoral offset; a medial posterior femoral offset; a lateral posterior femoral offset; a medial femoral offset at different flexion angles, e.g. at 20 degrees flexion or 30 degrees flexion; a lateral femoral offset at different flexion angles, e.g. at 20 degrees flexion or 30 degrees flexion; a medial femoral offset in hyperextension, e.g. in 5 degrees or 10 degrees of hyperextension; a lateral femoral offset in hyperextension, e.g. in 5 degrees or 10 degrees of hyperextension.

A computer processor can then, for example, orient and/or align one or more virtual implant components to be aligned in relationship to a predetermined or desired offset of the joint and/or the implant component. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is placed in relationship to a predetermined or desired offset, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the alignment in relationship to a predetermined or desired offset of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the alignment in relationship to a predetermined or desired offset of the one or more implant components in order to find a compromise between alignment in relationship to a predetermined or desired offset and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Femoral Component Flexion, Anterior Notching

In some embodiments, a computer processor can determine or can be used to determine and/or display an anterior cortex and/or the position of the anterior flange of the bone facing surface of the femoral component. The computer processor can determine or can be used to determine and/or can display any notching or impingement or diving of the anterior flange of the implant into the anterior cortex.

A computer processor can then, for example, orient and/or align one or more virtual implant components, e.g. a virtual femoral component, to be aligned in relationship to a predetermined or desired position and/or orientation of the implant component in relationship to the anterior cortex to avoid any notching or impingement or diving into the anterior cortex. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is placed in relationship to a predetermined or desired position or orientation to avoid notching or impingement or diving into the anterior cortex, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the position and/or orientation in relationship to a predetermined or desired position and/or orientation of the one or more implant components relative to the anterior cortex in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the position and/or orientation in relationship to the anterior cortex in order to find a compromise between position and/or orientation in relationship to a predetermined or desired position and/or orientation of the implant component relative to the anterior cortex and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Medial and/or Lateral Joint Line

In some embodiments, a computer processor can determine or can be used to determine and/or display the patient's medial and/or lateral joint line.

A computer processor can then, for example, orient and/or align one or more virtual implant components to be positioned, oriented and/or aligned in relationship to a predetermined or desired joint line of the joint and/or the implant component. The virtual implant component can be a 2D or 3D outline or placement indicator of the physical implant component. The virtual implant component can be a 3D display, optionally stereoscopic, of the physical implant. The virtual implant component can have one, two, or more dimensions or shape substantially similar to the physical implant component. The virtual implant component can be based on an STL file or file format. The virtual implant component can be based on a CAD file. The virtual implant component can be rendered by a graphics processor or other computer processor. The electronic file of the virtual implant component, e.g. an STL file, can be stored on storable media, e.g. RAM, hard disk, CR ROM, magnetic media.

Once the implant component is placed in relationship to a predetermined or desired joint line, a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the position, orientation and/or alignment in relationship to a predetermined or desired joint line of the joint or of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the position, orientation and/or alignment in relationship to a predetermined or desired joint line of the one or more implant components in order to find a compromise between alignment in relationship to a predetermined or desired joint line and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

Single, Multi-Parametric Fitting, Sizing, Shape Determination, Recommendation or Selection and/or Alignment In some embodiments, an implant component can be placed using two or more parameters, e.g. mechanical axis alignment or modifications thereof, rotation or rotation axis, slope, femoral offset, femoral component flexion, notching, medial and/or lateral joint line, alignment relative to one or more articular surface(s) (e.g. tangent or intersecting), e.g. a medial or latera femoral condyle. A computer processor can determine or help determine, e.g. using a user interface, a compromise between one or more of the foregoing parameters, implant fit, implant overhang, and/or implant undersizing. The virtual implant overhang, virtual implant oversizing, and/or virtual implant undersizing can be determined in relationship to an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, and any of the foregoing structures in a subsurface location. The virtual implant overhang, virtual implant oversizing, and/or virtual implant undersizing can be determined in relationship to an uncut bone surface and/or a cut bone surface. The term cut bone surface can include a bone surface that has been removed using a bone removal instrument such as a reamer, a mill, a broach. The virtual implant overhang, virtual implant oversizing, and/or virtual implant undersizing can be determined in relationship to an unaltered and/or a reamed acetabular surface or glenoid surface. The virtual implant overhang, virtual implant oversizing, and/or virtual implant undersizing can be determined in relationship to an uncut and/or a cut proximal femur, an uncut and/or a cut proximal humerus.

Non-limiting examples of parameters that can be used by a computer processor for determining at least one of a fit, a size, a shape or combinations thereof include, but are not limited to: a mechanical axis of a leg, a mechanical axis of a femur, a mechanical axis of a tibia, a rotation axis of a femur, a rotation axis of the tibia, an anatomic axis of the femur, an anatomic axis of the tibia, a biomechanical axis of the patella, a rotation axis of the patella, an anatomic axis of the patella, a transepicondylar line, a Whiteside's line, a medial joint line, a lateral joint line, a tibial slope, a tibial offset, a tibial plateau dimension, a tibial plateau perimeter, a dimension, a perimeter, a surface, a volume of a cut tibial plateau, a femoral offset, a femoral condyle, trochlea, distal femur dimension, a femoral perimeter, e.g. a perimeter of a femoral condyle, a dimension, a perimeter, a surface, a volume of a cut distal femur, e.g. a cut femoral condyle or a trochlea, or combinations thereof. The determining at least one of a fit, a size, a shape or combinations thereof can be automatic, e.g. using at least one computer processor and/or an ANN, semi-automatic, e.g. with some user assistance, or manual, e.g. using a graphical user interface controlled by at least one computer processor.

In some embodiments, the recommending and/or selecting of at least one of a size, fit, or shape (or combination thereof) of a virtual implant can be performed using a single parameter. In some embodiments, the recommending and/or selecting of at least one of a size, fit, or shape (or combination thereof) of a virtual implant can be performed using multiple parameters. The one or more parameters can be, for example, a fit in relationship to, a size in relationship to, a shape in relationship to, an alignment in relationship to at least one of an anatomic structure, an anatomic landmark, a mechanical axis of a leg, a mechanical axis of a femur, a mechanical axis of a tibia, a Whiteside's line, a transepicondylar line, a rotation axis of a femur, a rotation axis of the tibia, an anatomic axis of the femur, an anatomic axis of the tibia, a biomechanical axis of the patella, a rotation axis of the patella, an anatomic axis of the patella, an abduction axis or line, e.g. on the contact surface of two opposing articular surfaces, an adduction axis or line, e.g. on the contact surface of two opposing articular surfaces, a transepicondylar line, a Whiteside's line, a femoral, tibial, patellar contact surface or combinations thereof, a femoral, tibial, patellar contact line, or combinations thereof, a medial joint line, a lateral joint line, a tibial slope, a tibial offset, a tibial plateau dimension, a tibial plateau perimeter, a dimension, a perimeter, a surface, a volume of a cut tibial plateau, an anterior margin of a tibial plateau (before and/or after a bone removal, e.g. a bone cut or a burring), a posterior margin of a tibial plateau (before and/or after a bone removal, e.g. a bone cut or a burring), a medial margin of a tibial plateau (before and/or after a bone removal, e.g. a bone cut or a burring), a lateral margin of a tibial plateau (before and/or after a bone removal, e.g. a bone cut or a burring), a femoral condyle offset, a femoral condyle, a trochlea, a distal femoral dimension, a posterior femoral dimension, a femoral perimeter, e.g. a perimeter of a femoral condyle, a dimension, a perimeter, a surface, a volume of a cut distal femur, e.g. a cut femoral condyle or a trochlea, a medial, inferior, lateral, superior, anterior, posterior margin of a cut distal femur, e.g. a posterior femoral condyle, a dimension, an anterior femoral cortex, e.g. to avoid notching of a femoral component, a perimeter, a surface, a volume of an uncut or a cut or milled patella, a shape of a medial patellar facet, a shape of a lateral patellar facet, a shape of a patella, a trochlear sulcus, a trochlear sulcus line, a depth of a trochlear sulcus, a trochlear height, e.g. for assessing the fit, size, and/or shape of an anterior flange of a femoral component, a radius, a curvature, a shape of an articular surface, e.g. a femoral condyle, a tibial plateau, a patella, at least a portion of an internal or external margin, periphery, edge, perimeter, anteroposterior, mediolateral, oblique dimension, diameter, radius, curvature, geometry, shape or surface of one or more structures of a physical joint, e.g. a cortical bone, subchondral bone, cartilage, damaged or diseased cartilage, or combination thereof.

The one or more parameters can be, for example, at least one of a coordinate, a peripheral margin, a dimension, a shape, a radius, a convexity, a concavity of at least one of a medial wall of the femoral notch, a lateral wall of the femoral notch; a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau surface, a lateral tibial plateau surface, a medial tibial plateau surface, a lateral tibial plateau surface, any of the foregoing tissues and/or structures on a surgically exposed surface, any of the foregoing tissues and/or structures in a subsurface location or combinations thereof.

Anatomic structures or anatomic landmarks used for determining at least one of a fit, size shape or combination thereof and for recommending or selecting an implant component can comprise one or more of a:

Knee:

Medial wall of the femoral notch; Lateral wall of the femoral notch; Roof of the femoral notch Residual ACL origin; Residual ACL insertion; Medial wall of the medial condyle; Lateral wall of the lateral condyle; Medial epicondylar eminence; Lateral epicondylar eminence; Medial femoral condyle dimensions, shape, e.g. radii, convexities, concavities; Lateral femoral condyle dimensions, shape, e.g. radii, convexities, concavities; Posterior portion of medial femoral condyle including surface, peripheral margins, dimensions, shape, radii, convexities, concavities Posterior portion of lateral femoral condyle including surface, peripheral margins, dimensions, shape, radii, convexities, concavities; Central portion of medial femoral condyle including surface, peripheral margins, dimensions, shape, radii, convexities, concavities; Central portion of lateral femoral condyle including surface, peripheral margins, dimensions, shape, radii, convexities, concavities; Anterior portion of medial femoral condyle including surface, peripheral margins, dimensions, shape, radii, convexities, concavities; Anterior portion of lateral femoral condyle including surface, peripheral margins, dimensions, shape, radii, convexities, concavities; Intercondylar notch shape; Intercondylar notch surface features; Intercondylar notch ceiling; Intercondylar notch medial wall; Intercondylar notch lateral wall; Posterior portion of medial tibial plateau including surface, peripheral margins, dimensions, shape, radii, convexities, concavities; Posterior portion of lateral tibial plateau including surface, peripheral margins, dimensions, shape, radii, convexities, concavities; Central portion of medial tibial plateau including surface, peripheral margins, dimensions, shape, radii, convexities, concavities; Central portion of lateral tibial plateau including surface, peripheral margins, dimensions, shape, radii, convexities, concavities; Anterior portion of medial tibial plateau including surface, peripheral margins, dimensions, shape, radii, convexities, concavities; Anterior portion of lateral tibial plateau including surface, peripheral margins, dimensions, shape, radii, convexities, concavities; Medial tibial spine; Lateral tibial spine; Anteromedial tibial rim; Anterolateral tibial rim; Medial tibial rim; Lateral tibial rim; Lowest point of the medial plateau; Lowest point of the lateral plateau; Highest point of the medial plateau; Highest point of the lateral plateau; Medial tibial plateau surface, peripheral margins, dimensions, shape, radii, convexities, concavities; Lateral tibial plateau surface, peripheral margins, dimensions, shape, radii, convexities, concavities; Medial tibial plateau surface features, e.g. radii, convexities, concavities; Lateral tibial plateau surface features, e.g. radii, convexities, concavities; Tibial offset, i.e. offset between medial joint line and lateral joint line; Any of the foregoing tissues and/or structures on an exposed surface, e.g. surgically exposed; Any of the foregoing tissues and/or structures in a hidden location (e.g. unexposed by an incision) or a subsurface location; Any of the foregoing tissues and/or structures visualized using an imaging test, including, for example, x-rays with optionally 2D to 3D bone morphing to a 3D model, or combinations thereof.

Hip:

The one or more parameters can be, for example, at least one of a coordinate, a peripheral margin, a dimension, a shape, a radius, a convexity, a concavity of at least one of a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a fovea capitis, a transverse acetabular ligament, a pulvinar, a ligamentum teres, a labrum, one or more osteophytes, femoral and/or acetabular or combinations of any of the foregoing.

Shoulder:

The one or more parameters can be, for example, at least one of a coordinate, a peripheral margin, a dimension, a shape, a radius, a convexity, a concavity of at least one of a portion or an entire glenoid; a portion or an entire coracoid process, a portion or an entire acromion, a portion of a clavicle, a portion or an entire humeral head, a portion or an entire humeral neck, a portion of a humeral shaft, one or more humeral osteophytes, one or more glenoid osteophytes, a portion or an entire glenoid labrum, a portion or an entire shoulder ligament, e.g. a coracoacromial ligament, a superior, middle, or inferior glenohumeral ligament, a portion of a shoulder capsule or combinations of any of the foregoing.

Optionally, in any of the embodiments, a computer processor can align one or more virtual implant components, including virtual implant components on opposing articular surface or articulating articular surfaces in relationship to at least one of a mechanical axis, a rotation axis, a transepicondylar axis, a Whiteside's line, a tibial slope, a femoral offset, a tibial offset, i.e. the offset between the medial and the lateral joint line, a femoral component flexion, an anterior notching, an anterior cortex, a medial joint line, a lateral joint line or combinations thereof. The aligning of the virtual implant component can be automatic, e.g. using at least one computer processor and/or an ANN, semi-automatic, e.g. with some user assistance, e.g. using a graphical user interface controlled by at least one computer processor, or manual, e.g. using a graphical user interface controlled by at least one computer processor. The computer processor and/or the ANN can use a single parameter or multiple parameters for aligning the virtual implant component, e.g. at least one of a mechanical axis, a rotation axis, a transepicondylar axis, a Whiteside's line, a tibial slope, a femoral offset, a tibial offset, i.e. the offset between the medial and the lateral joint line, a femoral component flexion, an anterior notching, an anterior cortex, a medial joint line, a lateral joint line or combinations thereof.

Once the implant component has placed in relationship to a predetermined or desired parameter or set of parameter(s) (e.g. any of the foregoing parameters), a computer processor can evaluate or can be used to evaluate the fit of the implant component relative to the underlying bone, e.g. uncut bone or cut bone, drilled bone, burred bone, milled bone, reamed bone, impacted bone (any form of bone removal is applicable), and relative to the perimeter or edge or margin of the bone, e.g. before or after bone removal. Optionally, the operator or computer processor can modify the position, orientation and/or alignment in relationship to a predetermined or desired parameter(s) (e.g. any of the foregoing parameters) of the one or more implant components in order to optimize the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal. Optionally, the operator or computer processor can modify the position, orientation and/or alignment in relationship to a predetermined or desired parameter(s) (e.g. any of the foregoing parameters) of the one or more implant components in order to find a compromise between position, orientation, and/or alignment in relationship to a predetermined or desired parameter(s) and the fit relative to the underlying bone, e.g. uncut bone or cut bone, drilled bone, burred bone, milled bone, reamed bone, impacted bone (any form of bone removal is applicable), and/or relative to the perimeter or edge or margin of the bone, e.g. before or after bone removal.

2D Imaging

Any of the foregoing parameter(s) and additional parameters, e.g. in other joints, e.g. the shoulder, hip or ankle joint, can be derived using x-ray images, e.g. AP, lateral and/or oblique, of the patient, e.g. supine or upright or obtained during stress testing. 2D imaging can be used in conjunction with any of the embodiments described in the specification. 2D imaging can be combined with 3D imaging.

3D Imaging

Any of the foregoing parameter(s) and additional parameters, e.g. in other joints, e.g. the shoulder, hip or ankle joint, can be derived using 3D imaging studies, e.g. ultrasound, CT or MRI and, in some embodiments, 3D imaging using 3D scanners or laser scanners. 3D imaging can be used in conjunction with any of the embodiments described in the specification. 3D imaging can be combined with 2D imaging.

Bone Morphing, Cartilage Morphing

In some embodiments, the shape of one or more of the patient's tissues, such as a bone, a cartilage, can be estimated or morphed based on 2D imaging or 2D data, optionally obtained from multiple view angles or perspectives or projections. The estimating or morphing of the patient's tissue shape, e.g. bone shape, cartilage shape, can help reduce or obviate the need for 3D imaging.

In some embodiments, 2D preoperative data can be used and the shape of one or more of the patient's tissues, such as a bone, a cartilage, can be estimated or morphed in three dimensions pre-operatively, e.g. prior to surgery.

Bone Morphing and/or Cartilage and/or Tissue Morphing Using Pre-Operative Imaging In some embodiments, one or more two-dimensional images of the patient can be obtained. These images can, for example, include one or more x-rays of the patient. X-rays can be obtained using digital acquisition techniques. X-rays can also be obtained using conventional film based technique, in which case the x-rays can be subsequently digitized using a scanner.

Exemplary x-ray images can include:
- Spine: AP, PA, lateral, oblique views, and/or angled views, flexion, extension views, lateral bending views; upright, supine or prone
- Hip: AP, PA, lateral, oblique views, angled views, and/or frogleg view; standing or lying, weight-bearing or non-weight-bearing
- Knee: AP, PA, lateral, oblique views, angled views, tunnel view, and/or Merchant view, sunrise view and the like, any other patellar, femoral or tibial views known in the art; standing or lying, weight-bearing or non-weight-bearing
- Shoulder: AP, PA, lateral, axillary view trans-scapular Y view, etc.
- Full leg x-rays films; standing or lying, weight-bearing or non-weight-bearing
- Full femur x-rays; standing or lying, weight-bearing or non-weight-bearing
- Full tibia x-rays; standing or lying, weight-bearing or non-weight-bearing
- Selective leg x-rays films, e.g. hip, knee, ankle; standing or lying, weight-bearing or non-weight-bearing X-rays can be obtained with the patient in upright, supine and/or prone position. X-rays can be obtained with the patient in weight-bearing and in non-weight-bearing position. In some embodiments, x-rays are obtained intra-operatively, for example with the patient already positioned and placed for the intended surgical procedure.

The x-ray data of the patient can be transferred into a computer. Optionally, a computer processor can apply image processing to segment select patient tissues, such as a bone or vertebra or vertebral structure, subchondral bone, cortical bone, osteophytes. Image processing can, for example, also be applied to determine the edge of select patient tissues, such as a bone or vertebra or vertebral structure, subchondral bone, cortical bone, osteophytes. When subchondral bone has been identified and/or derived from the images, including a subchondral bone curvature and/or geometry and/or shape, a cartilage shape, curvature or geometry can be superimposed or added to the subchondral bone shape. The cartilage shape, curvature or geometry can assume a standard cartilage thickness for a given joint and/or a given patient, e.g. 1.0 mm, 1.5 mm, 2.0 mm, 2.5 mm, 3.0 mm, 3.5 mm. The cartilage geometry can also assume a variable cartilage thickness, e.g. depending on the location of the cartilage in the joint and/or on the articular surface and/or based on the patient's age, gender, race, body weight, and/or BMI, as well as underlying deformity, e.g. varus or valgus deformity.

In some embodiments, the 2D x-rays images can be used to derive information about the dimensions and 3D shape of the anatomic structure(s) included in the x-ray. Some of this information can be, for example:
- Anatomic landmark(s)
- Distances and/or dimensions between two or more known landmarks/structures
- Angles between landmarks
- Anatomic axes
- Biomechanical axes
- Curvature information
- Curvature information of a bone surface
- Curvature information of a subchondral bone surface
- Curvature information of an articular surface
- Change in curvature from convex to concave
- Change in curvature from concave to convex
- Surface information
- Edge information
- Shape information, e.g. when information from multiple x-rays images obtained with different projection or beam angles is combined or aggregated
- Length information, e.g. in AP, ML, SI direction, AP, ML, SI plane, oblique planes
- Width information, e.g. in AP, ML, SI direction, AP, ML, SI plane, oblique planes
- Depth information, e.g. in AP, ML, SI direction, AP, ML, SI plane, oblique planes Any of the foregoing information can be external on the surgical field, e.g. directly visible to the eye of a surgeon and/or on an accessible surface. Any of the information can be internal to the surgical field, e.g. not directly visible to the eye of a surgeon and/or not on an accessible surface and/or hidden by other tissue, e.g. bone, cortical bone and/or soft-tissue.

Examples of landmarks, distances, dimensions, surfaces, edges, angles, axes, curvatures, shapes, lengths, widths, depths and/or other features for the spine, the hip, the knee and the shoulder joint that can be used for bone morphing and 3D model selection, development, derivations, and deformations in any surgeries of these or to these areas are provided below in Table 1. These examples are in no way meant to be limiting of the disclosure, but are only exemplary in nature. Other landmarks, distances, dimensions, surfaces, edges, angles, axes, curvatures, shapes, lengths, widths, depths and/or other features for these joints as well as any other joint in the human body can be used.

For any of the embodiments, landmarks, distances, dimensions, surfaces, edges, angles, axes, curvatures, shapes, lengths, widths, depths and/or other features can be external on the surgical field, e.g. on an accessible surface; landmarks, distances, dimensions, surfaces, edges, angles, axes, curvatures, shapes, lengths, widths, depths and/or other features can be internal to the surgical field, e.g. not on an accessible surface and/or hidden by other tissue, e.g. bone, cortical bone and/or soft-tissue.

TABLE 1. Examples of landmarks, distances, dimensions, surfaces, edges, angles, axes, curvatures, shapes, lengths, widths, depths and/or other features for the spine, the hip, the knee and the shoulder joint that can be used for bone morphing and 3D model selection, development, derivations, and deformations in any surgeries of these or to these areas.

Spine:

Cortical bone of a pedicle; Endosteal bone of a pedicle; Posterior cortical bone of a vertebral body; Anterior cortical bone of a vertebral body; Lateral cortical bone of a vertebral body; Superior endplate; Inferior endplate; Intervertebral disk; Vertebral body; Trabecular bone of the vertebral body; Superior facet; Inferior facet; Spinous process; Any fracture components or fragments, e.g. involving a pedicle, a facet joint or a vertebral body; Endplate shape, e.g. sagittal plane; Endplate shape, e.g. coronal plane; Schmorl's node(s); Interpedicular distance; Intervertebral height or disk height; AP length of vertebral body, e.g. at level of inferior endplate, superior endplate, mid-portion; ML width of vertebral body, e.g. at level of inferior endplate, superior endplate, mid-portion; Oblique width vertebral body, e.g. at level of inferior endplate, superior endplate, mid-portion; Vertebral body height, e.g. anterior, mid-portion, posterior; Pedicle length; Pedicle width; Pedicle height; Pedicle angle; Spinous process SI thickness, e.g. anterior, mid-portion, tip; Spinous process width, e.g. anterior, mid-portion, tip; Spinous process inferior angle from origin; Facet dimensions, AP, ML, SI; Facet angle, e.g. angle of joint formed between inferior facet of superior vertebra and superior facet of inferior vertebra; Lamina SI height; Lamina AP width; Lamina ML radius, diameter; Spinal canal AP diameter, ML diameter; Lordosis; Kyphosis; Scoliosis; Side bending, e.g. left lateral, right lateral; Cobb angle; Lumbosacral angle Hip:

Lateral acetabular point or edge; Medial acetabular point or edge; Superior acetabular point or edge; Anterior acetabular point or edge; Posterior acetabular point or edge; Triradiate cartilage and region; Acetabular labrum, medial, lateral, anterior, posterior (e.g. when x-ray contrast has been injected into the joint); Fovea capitis; Femoral head subchondral bone, contour, outline; Femoral head-neck/junction, curvature, convex, concave; Greater trochanter, e.g. lateral cortex, superior cortex, anterior cortex, posterior cortex; Sulcus point (lowest point between greater trochanter and femoral neck), e.g. as seen on a frontal or AP x-ray; Sulcus curvature; Greater trochanter/sulcus transition, curvature, convex, concave; Lesser trochanter; Lesser trochanter/femoral neck transition, curvature; Lesser trochanter/femoral shaft transition; Femoral shaft, anterior cortex, posterior cortex, medial cortex, lateral cortex; Anterior cortex, posterior cortex, medial cortex, lateral cortex for any of the foregoing structures as applicable; Endosteal bone, anterior, posterior, medial, lateral for any of the foregoing structures as applicable; Femoral neck angle; Femoral shaft angle; Acetabular angle; Acetabular anteversion; Femoral anteversion; Femoral shaft angle; Pelvic tilt; Femoral offset; Shenton's line; Hilgenreiner line; Perkin line; Acetabular index Knee:

Medial wall of the femoral notch; Lateral wall of the femoral notch; Roof of the femoral notch; Femoral notch geometry; Femoral notch shape; Distance/line/plane from roof of femoral notch to lowest point or other point or surface on medial femoral condyle; Distance/line/plane from roof of femoral notch to lowest point or other point or surface on lateral femoral condyle; Medial wall of the medial condyle; Lateral wall of medial condyle; Medial wall of lateral condyle; Lateral wall of the lateral condyle; Medial edge of the medial condyle; Lateral edge of medial condyle; Medial edge of lateral condyle; Lateral edge of the lateral condyle; Medial edge of the medial condyle after one or more more bone resections or bone removals; Lateral edge of medial condyle after one or more more bone resections or bone removals; Medial edge of lateral condyle after one or more more bone resections or bone removals; Lateral edge of the lateral condyle after one or more more bone resections or bone removals; Medial epicondylar eminence; Lateral epicondylar eminence; Medial femoral condyle shape, e.g. radii, convexities, concavities, curvatures, e.g. sagittal J-curve; Lateral femoral condyle shape, e.g. radii, convexities, concavities curvatures, e.g. sagittal J-curve; Intercondylar notch shape; Intercondylar notch surface features; Medial tibial spine; Lateral tibial spine; Anteromedial tibial rim; Anterolateral tibial rim; Medial tibial rim; Lateral tibial rim; Posterior tibial rim; Anteromedial tibial edge; Anterolateral tibial edge; Medial tibial edge; Lateral tibial edge; Posterior tibial edge; Anteromedial tibial edge after one or more more bone resections or bone removals; Anterolateral tibial edge after one or more more bone resections or bone removals; Medial tibial edge after one or more more bone resections or bone removals; Lateral tibial edge after one or more more bone resections or bone removals; Posterior tibial edge after one or more more bone resections or bone removals; Lowest point of the medial plateau; Lowest point of the lateral plateau; Highest point of the medial plateau; Highest point of the lateral plateau; Medial tibial plateau shape; Lateral tibial plateau shape; Medial tibial plateau sagittal curvature; Lateral tibial plateau sagittal curvature; Medial tibial plateau coronal curvature; Lateral tibial plateau coronal curvature; Medial tibial plateau surface features, e.g. radii, convexities, concavities; Lateral tibial plateau surface features, e.g. radii, convexities, concavities; Femoral osteophytes; Tibial osteophytes; Patellar osteophytes; Femoral subchondral cysts; Tibial subchondral cysts; Patellar osteophytes; Patellar subchondral cysts; Trochlea osteophytes; Trochlea subchondral cysts; Patellar sagittal curvature; Patellar coronal curvature; Patellar axial curvature; Patellar surface features, e.g. radii, convexities, concavities; Patellar surface features, e.g. radii, convexities, concavities; Patellar circumference shape; Patellar rise; Patellar thickness; Trochlear depth; Trochlear sagittal curvature; Trochlear axial curvature; Trochlear coronal curvature; Trochlea sagittal shape; Trochlea axial shape; Trochlea coronal shape; Trochlear angle; Trochlear sulcus depth; Epicondylar axis; Posterior femoral axis; Trochlear rotation axis; Mechanical axis; Q-angle Shoulder:

Clavicle; AC joint; Acromion; Glenoid; Scapula; Coracoid; Humeral head; Humeral neck; Humeral shaft; Glenoid osteophytes; Humeral osteophytes; AC joint osteophytes; Glenoid subchondral cysts; Humeral subchondral cysts; AC joint subchondral cysts; Acromio-humeral distance; Acromio-humeral space; Deepest point of glenoid; Most anterior point or edge of glenoid; Most posterior point or edge of glenoid; Most superior point or edge of glenoid; Most inferior point or edge of glenoid; Glenoid shape; Humeral head shape; Glenoid sagittal curvature, e.g. radii, convexities, concavities; Glenoid axial curvature, e.g. radii, convexities, concavities; Glenoid coronal curvature, e.g. radii, convexities, concavities; Humeral head sagittal curvature, e.g. radii, convexities, concavities; Humeral head axial curvature, e.g. radii, convexities, concavities; Humeral head coronal curvature, e.g. radii, convexities, concavities; Mechanical axis; Anatomical axis; Angle of inclination; Axis of head and neck; Axis through epicondyles; Angle of retroversion. These landmarks, distances, dimensions, surfaces, edges, angles, axes, curvatures, shapes, lengths, widths, depths and/or other features for the spine, the hip, the knee and the shoulder joint can also be used for the virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member. These landmarks, distances, dimensions, surfaces, edges, angles, axes, curvatures, shapes, lengths, widths, depths and/or other features for the spine, the hip, the knee and the shoulder joint can also be used for other applications throughout the application that utilize anatomic information, e.g. measurements, developments of virtual surgical plans.

By measuring any of the foregoing landmarks, distances, dimensions, surfaces, edges, angles, axes, curvatures, shapes, lengths, widths, depths and/or other features, including external on the surgical field, e.g. directly visible to the eye of a surgeon and/or on an accessible surface and/or internal to the surgical field, e.g. not directly visible to the eye of a surgeon and/or not on an accessible surface and/or hidden by other tissue, e.g. bone, cortical bone and/or soft-tissue, it is possible to estimate a 3D shape, volume or surface(s) of a bone, e.g. a proximal femur, a distal femur, a proximal tibia, an acetabulum, a vertebral body and spinal elements and a glenoid and/or a proximal humerus. The more landmarks, distances, dimensions, surfaces, edges, angles, axes, curvatures, shapes, lengths, widths, depths and/or other features are being measured, the more accurate can the estimation of the 3D shape, volume or surface(s) of the bone be. In addition, the more 2D images are being taken or acquired from different view angles, projection angles, beam angles, optionally with the same magnification or different magnifications, optionally with or without magnification correction applied, the more accurate can the estimation of the 3D shape, volume or surface(s) of the bone be.

The 3D shape, volume or surface or curvature of the bone can, for example, be estimated by filling in the information, e.g. intermediate or connecting landmarks, distances, dimensions, surfaces, edges, angles, axes, curvatures, shapes, lengths, widths, depths and/or other features between known landmarks, distances, dimensions, surfaces, edges, angles, axes, curvatures, shapes, lengths, widths, depths and/or other features derived from the one, two, three or more x-ray images. The 3D shape, volume or surface or curvature of the bone can, for example, be estimated by interpolating surfaces between multiple points or by fitting splines.

In some embodiments, a standard model of the bone can be used and can be deformed using one or more of the known landmarks, distances, dimensions, surfaces, edges, angles, axes, curvatures, shapes, lengths, widths, depths and/or other features derived from the x-ray images, including using landmarks, distances, dimensions, surfaces, edges, angles, axes, curvatures, shapes, lengths, widths, depths and/or other features external on the surgical field, e.g. directly visible by the eye of a surgeon and/or on an accessible surface and/or landmarks, distances, dimensions, surfaces, edges, angles, axes, curvatures, shapes, lengths, widths, depths and/or other features internal to the surgical field, e.g. not directly to the eye of a surgeon and/or not on an accessible surface and/or hidden by other tissue, e.g. bone, cortical bone and/or soft-tissue. Such deformations can be performed using various statistical models known in the art.

In some embodiments, a database or library of bone models and tissue models can be used. The one or more of these anatomic landmarks, distances, dimensions, surfaces, edges, angles, axes, curvatures, shapes, lengths, widths, depths and/or other features, e.g. external or internal, can be used to identify a standard bone shape and/or a standard cartilage shape by comparing the one or more landmarks, distances, dimensions, surfaces, edges, angles, axes, curvatures, shapes, lengths, widths, depths and/or other external or internal features with data in a reference database of reference patients and/or reference bone and/or cartilage shapes and by selecting a 3D model that most closely matches the selected landmarks, distances, dimensions, surfaces, edges, angles, axes, curvatures, shapes, lengths, widths, depths and/or other features. In this manner, the 3D shape of the patient's bones and/or cartilage, e.g. the distal femur and/or the proximal tibia and/or the acetabulum and/or the proximal femur, and/or the vertebral body and/or the spinal elements and/or the glenoid and/or the proximal humerus, can be estimated without the need acquire 3D data or without the need of segmentation of the 3D data or limiting the amount of segmentation needed from available 3D data, e.g. a CT scan or an MRI scan of the patient. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement. Such scan data can be used to generate a database of 3D shapes of patients with different age, gender, ethnic background, race, weight, height and/or BMI.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment of the disclosure throughout the specification including for all other clinical applications, e.g. hip replacement, knee replacement, shoulder replacement spinal surgery, spinal fusion, vertebroplasty, kyphoplasty, ACL repair, ACL reconstruction, fracture fixation.

In some embodiments, a standard model, optionally already deformed using the patient's landmarks, distances, dimensions, surfaces, edges, angles, axes, curvatures, shapes, lengths, widths, depths and/or other features, can be combined or fused with a model selected from a database using the patient's landmarks, distances, dimensions, surfaces, edges, angles, axes, curvatures, shapes, lengths, widths, depths and/or other features. In some embodiments, the model selected from the database can be deformed and/or adapted using the patient's landmarks, distances, dimensions, surfaces, edges, angles, axes, curvatures, shapes, lengths, widths, depths and/or other features. Such deformations can be performed using various statistical models known in the art.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other landmarks, distances, dimensions, surfaces, edges, angles, axes, curvatures, shapes, lengths, widths, depths and/or other features, e.g. external or internal, can be identified.

A lateral knee x-ray can, for example, be used to derive curvature information about the medial and the lateral condyle. Two distinct curves can be seen on a lateral knee radiograph, one representing the medial condyle and the other representing the lateral condyle. In most instances, the lateral condyle has a smaller radius than the medial condyle, for example in the central weight-bearing zone. Software can identify and/or segment each curve using, for example, some of the software packages described in U.S. Pat. No. 9,861,446, which is incorporated herein by reference in its entirety. This can be followed by a curvature analysis assessing the radii of each curve. In some embodiments, the curve with the smaller radii, e.g. in the central weight bearing area, can be assigned as the lateral condyle. Other combinations are possible. If the position of the leg is known relative to the x-ray source and detector panel, e.g. medial side or lateral side of the knee closer to the detector panel, e.g. with lower magnification, the dimensions or magnification of a first condyle can be compared to the dimensions or magnification of the second condyle and the difference in measured dimensions, and, optionally, estimated magnification, can be used to identify the condyle closer to the detector panel on the x-ray, e.g. less magnified, and the condyle further away from the detector panel, e.g. more magnified. The identification of the medial and/or lateral condyle can be manual, e.g. by the operator or surgeon, semi-automatic or automatic.

The foregoing description of techniques to estimate or morph the three-dimensional shape of a patient's bone is only exemplary in nature and is in no way meant to be limiting of the disclosure. Someone skilled in the art will readily recognize other means to estimate the shape of the patient's bone in three dimensions. Any technique known in the art for determining or estimating the three-dimensional shape of a bone from two-dimensional data can be used. Any technique known in the art for modeling and displaying the three-dimensional shape of a bone from two-dimensional data can be used. The resultant 3D model of the patient's bone using any of these techniques can then be displayed by one or more computer monitors.

Libraries of Virtual Implant Components

In some embodiments, one or more libraries of virtual implant components can be used based on one or more existing total knee systems. Virtual implant components can, for example, be stored on computer storage media, or used in the form of CAD files, for example in SolidWorks format (DS Solid Works Corporation, Waltham, Mass., USA). The CAD files can be converted into Wavefront Object file format (*.obj) for display by a standard computer interface and display by one or more computer monitors. Each Solidworks file can have a unique identifier for a given size, shape, and/or laterality of an implant component, which can, for example, correspond to a unique QR code for inventory management and invoicing. The one or more libraries of virtual implant components can include existing sizes and shapes from multiple manufacturers, including symmetric and asymmetric femoral and/or tibial and/or patellar components, components with offsets, and/or implant components of any other joint.

3D Morphing of Implant Components from 2D Templates

When STL or CAD files of implant components of different manufacturers are not available, using screen capture of the radiographic template of the patient, 2D templates can be imported by a computer processor using software which can be based, for example, on the OrthoTAIX ESPP System (SurgiTAIX AG, Herzogenrath, Germany). The following parameters can be, for example, detected on the 2D CAD files using the example of a knee replacement system: maximum thickness between distal femoral cut and distal femoral bearing surface on AP (anterior-posterior) view, maximum thickness between distal femoral cut and distal femoral bearing surface on lateral view, peg length, peg angle, peg location, length of distal cut planar surface on AP view for medial and lateral condyle, length of distal cut planar surface on lateral view, length and angle relative to distal cut of anterior chamfer cut on lateral view, length and angle relative to anterior chamfer cut of anterior cut on lateral view, length and angle of posterior chamfer cuts relative to distal cut on lateral view, length and angle relative to posterior chamfer cuts of posterior cuts on lateral view, and curvature of central femoral bearing surface on lateral view. Similar information can be obtained on the tibial side. The measurements can be used to deform a standard 3D CAD file of a distal femoral component or a proximal tibial component. For this purpose, a pre-defined set of 3D landmarks can be assigned to the standard implant surface for both femoral and tibial components (e.g. so-called "template set"). On the available 2D screen captures (AP, lateral, other views), a similar set of landmarks (so-called "target set") can be identified. The deformation of the standard 3D CAD surface can be carried out by mapping the "template set" to the "target set" using one or more non-linear scaling transformations. The transformation of all remaining points of the 3D CAD surface model can be approximated using, for example, Radial Basis Functions (RBFs). The RBFs can be useful in a matching case since they can provide interpolants to values given at irregularly positioned points and since they can work well even for small landmark sets.

The deformation can account for the principal dimensions of different implant systems that are used to derive their cut planes or bone removal areas. Optionally, a calibration phantom of known size and dimensions can be included on the patient's x-rays to allow for magnification correction and/or adjustment. The calibration phantom can be used to adjust or scale for any x-ray magnification.

Bone Cuts, Bone Removal 2D implant templates can be morphed into 3D implant shapes and/or shapes and/or placement indicators using any of the embodiments in the specification. 3D implant files, e.g. CAD files or STL files from a library of implants, can be used in any of the embodiments of the specification. The 2D implant templates or 3D implant shapes (morphed from 2D templates or obtained from a 3D CAD file or STL file) can be used to determine the amount of bone removal and to determine one or more bone surfaces after bone removal on which an implant can be fitted, e.g. in a virtual surgical plan using, for example, a 3D model or 3D surface of the bone (before and/or after bone removal) generated from a 3D scan or 2D x-rays using bone morphing. With the amount of bone removal, e.g. from cutting, drilling, burring, milling, sawing, reaming, broaching and/or impacting, known and the geometry of the altered bone surface, e.g. prepared for implantation of the implant component, known, the amount of bone coverage (e.g. dimensions, area, volume) can be determined for a given virtual (and/or physical) implant component. Similarly, a computer processor can be used to determine any overhang or undersizing of a virtual implant component. The computer processor can be used to identify areas of implant overhang and/or undersizing and the computer processor can help determine the amount of overhang or undersizing in a given area or across the entire surface of the bone prepared for implantation.

Determination of Implant Overhang Implant Undersizing, Bone Coverage, e.g. Femoral or Tibial Bone Overhang, Undersizing, Bone Coverage In some embodiments, a processor can be configured to facilitate simultaneous or sequential display of two or more virtual implant components with different sizes or shapes and the processor can be configured to receive input from a user interface to facilitate assessment of the fit and/or alignment of the two or more virtual implants to the surgical site of the patient, e.g. a cut bone, a drilled bone, a burred bone, a milled bone, a reamed bone, a broached bone and/or an impacted bone.

In some embodiments, a first user interface can be used to facilitate the placing of a virtual surgical guide, a virtual tool, a virtual instrument and/or a virtual implant or implant component, e.g. a knee, hip, ankle, shoulder, spinal implant component or other implant component. A second user interface can be used to facilitate the moving of a virtual surgical guide, a virtual tool, a virtual instrument and/or a virtual implant or implant component, e.g. a knee, hip, ankle, shoulder, spinal, dental implant component or other implant component. A third user interface can be used to facilitate the orienting of a virtual surgical guide, a virtual tool, a virtual instrument and/or a virtual implant or implant component, e.g. a knee, hip, ankle, shoulder, spinal, dental implant component or other implant component. A fourth user interface can be used to facilitate the aligning of a virtual surgical guide, a virtual tool, a virtual instrument and/or a virtual implant or implant component, e.g. a knee, hip, ankle, shoulder, spinal, dental implant component or other implant component. A fifth user interface can be used to facilitate the fitting of a virtual implant or implant component, e.g. a knee, hip, ankle, shoulder, spinal implant component or other implant component. A sixth user interface can be used to facilitate the sizing of a virtual implant or implant component, e.g. a knee, hip, ankle, shoulder, spinal, dental implant component or other implant component. A seventh user interface can be used to facilitate the selection of a virtual implant or implant component, e.g. a knee, hip, ankle, shoulder, spinal, dental implant component or other implant component.

The first user interface can be the same or different than the second, third, fourth, fifth, sixth or seventh user interface; the second user interface can be the same or different than the first, third, fourth, fifth, sixth or seventh user interface; the third user interface can the same or different than the first, second, fourth, fifth, sixth and seventh user interface; the fourth user interface can be the same or different than the first, second, third, fifth, sixth or seventh user interface; the fifth user interface can be the same or different than the first, second, third, fourth, sixth or seventh user interface; the sixth user interface can be the same or different than the first, second, third, fourth, fifth or seventh user interface; the sixth user interface can be the same or different than the first, second, third, fourth, fifth or sixth user interface.

In some embodiments, a first computer processor can be used to facilitate the placing of a virtual surgical guide, a virtual tool, a virtual instrument and/or a virtual implant or implant component, e.g. a knee, hip, ankle, shoulder, spinal implant component or other implant component. A second computer processor can be used to facilitate the moving of a virtual surgical guide, a virtual tool, a virtual instrument and/or a virtual implant or implant component, e.g. a knee, hip, ankle, shoulder, spinal implant component or other implant component. A third computer processor can be used to facilitate the orienting of a virtual surgical guide, a virtual tool, a virtual instrument and/or a virtual implant or implant component, e.g. a knee, hip, ankle, shoulder, spinal, dental implant component or other implant component. A fourth computer processor can be used to facilitate the aligning of a virtual surgical guide, a virtual tool, a virtual instrument and/or a virtual implant or implant component, e.g. a knee, hip, ankle, shoulder, spinal implant component or other implant component. A fifth computer processor can be used to facilitate the fitting of a virtual implant or implant component, e.g. a knee, hip, ankle, shoulder, spinal implant component or other implant component. A sixth computer processor can be used to facilitate the sizing of a virtual implant or implant component, e.g. a knee, hip, ankle, shoulder, spinal implant component or other implant component. A seventh computer processor can be used to facilitate the selection of a virtual implant or implant component, e.g. a knee, hip, ankle, shoulder, spinal implant component or other implant component. The first, second, third, fourth, fifth, sixth and seventh computer processor can be the same or different.

The first computer processor can be the same or different than the second, third, fourth, fifth, sixth or seventh computer processor; the second computer processor can be the same or different than the first, third, fourth, fifth, sixth or seventh computer processor; the third computer processor can the same or different than the first, second, fourth, fifth, sixth and seventh computer processor; the fourth computer processor can be the same or different than the first, second, third, fifth, sixth or seventh computer processor; the fifth computer processor can be the same or different than the first, second, third, fourth, sixth or seventh computer processor; the sixth computer processor can be the same or different than the first, second, third, fourth, fifth or seventh computer processor; the sixth computer processor can be the same or different than the first, second, third, fourth, fifth or sixth computer processor.

Using, for example, a display and one or more computer processors generating the display, the surgeon and/or the computer processor can evaluate the fit of the virtual implant, virtual implant component and/or virtual medical device and/or virtual instrument and can visually select a good or best fitting virtual implant, virtual implant component and/or virtual medical device in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal). The virtual fitting and/or selecting a good or best fitting virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal).

Using, for example, a display and one or more computer processors generating the display, the surgeon and/or the computer processor can evaluate the shape of a virtual implant, virtual implant component and/or virtual medical device and/or virtual instrument and can visually select the virtual implant, virtual implant component and/or virtual medical device with regard to its shape in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal). The virtual evaluation of the shape of a virtual implant, virtual implant component and/or virtual medical device can be based on a single or a multiple parameters, i.e. can be single or multi-parametric, e.g. by evaluating, assessing, considering, using any one or more of the exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal) including any of the anatomic structures, landmarks etc. mentioned in the specification.

Using, for example, a display and one or more computer processors generating the display, the computer processor can also determine the preferred position and/or orientation and/or alignment of the virtual implant, virtual implant component and/or virtual medical device and/or virtual instrument in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more bone surface, e.g. implant facing bone surfaces, e.g. cut or uncut, and/or one or more margins, edges, and/or perimeters of a cut or uncut bone surface (including virtual cuts or bone removal). The virtual determining of a preferred position and/or orientation and/or alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site, and/or one or more bone surface, e.g. implant facing bone surfaces, e.g. cut or uncut, and/or one or more margins, edges, and/or perimeters of a cut or uncut bone surface (including virtual cuts or bone removal).

Using, for example, a display and one or more computer processors generating the display, the surgeon and/or the computer processor can determine the preferred alignment of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more bone surface, e.g. implant facing bone surfaces, e.g. cut or uncut, and/or one or more margins, edges, and/or perimeters of a cut or uncut bone surface (including virtual cuts or bone removal). The virtual aligning and/or virtual evaluation of the alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal).

Using, for example, a display and one or more computer processors generating the display, the surgeon and/or the computer processor can determine the preferred function of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site, and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more bone surfaces, e.g. implant facing bone surfaces, e.g. cut or uncut, and/or one or more margins, edges, and/or perimeters of a cut or uncut bone surface (including virtual cuts or bone removal), and/or one or more functional tests, which can include any of these parameters and the virtual implant, virtual implant component and/or virtual medical device and virtual instrument. The virtual determining of the preferred function of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site, and/or one or more bone surfaces, e.g. implant facing bone surfaces, e.g. cut or uncut, and/or one or more margins, edges, and/or perimeters of a cut or uncut bone surface (including virtual cuts or bone removal), and/or one or more functional tests, which can include any of these parameters and the virtual implant, virtual implant component and/or virtual medical device and virtual instrument.

Using, for example, a display and one or more computer processors generating the display, the surgeon and/or the computer processor can determine and/or select a preferred virtual anchor, attachment or fixation member for the virtual implant, virtual implant component and/or virtual medical device and virtual instrument, in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more bone surfaces, e.g. implant facing bone surfaces, e.g. cut or uncut, and/or one or more margins, edges, and/or perimeters of a cut or uncut bone surface (including virtual cuts or bone removal), for example when simultaneously projecting a registered and superimposed imaging study of the patient, e.g. an x-ray, an ultrasound, a CT, an MRI or a PET scan, e.g. for demonstrating underlying tissue such as bone and bone stock. The virtual determination and/or virtual selection of a preferred virtual anchor, attachment or fixation member of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, bone stock, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site and/or one or more bone surface, e.g. implant facing bone surfaces, e.g. cut or uncut, and/or one or more margins, edges, and/or perimeters of a cut or uncut bone surface (including virtual cuts or bone removal).

Using, for example, a display and one or more computer processors generating the display, the surgeon and/or the computer processor can determine if portions of a virtual implant component overhang the bone, e.g. uncut bone or bone prepared for accepting an implant. The bone can be prepared in a computer simulation to accept the bone, for example by simulating one or more of a bone cut, a drilling, a burring, a milling, a reaming, a broach and/or an impact and/or any other type of bone removal known in the art. If portions of a virtual implant component overhang the bone in select areas, the amount of overhang can be determined, for example as a distance measurement, e.g. in mm, or an area measurement. If a distance measurement is used, it can be, for example a maximum overhang or an average overhang. If an area measurement is used, it can be a measurement, for example, in $mm^2$ indicating, for example, the total area of implant overhanging the bone.

The virtual implant overhang, virtual implant oversizing, and/or virtual implant undersizing can be determined by the computer processor in relationship to an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, any of the foregoing structures on a surgically exposed surface, and any of the foregoing structures in a subsurface location. The virtual implant overhang, virtual implant oversizing, and/or virtual implant undersizing can be determined in relationship to an uncut bone surface and/or a cut bone surface. The term cut bone surface can include a bone surface that has been removed using a bone removal instrument such as a reamer, a mill, a broach. The virtual implant overhang, virtual implant oversizing, and/or virtual implant undersizing can be determined in relationship to an unaltered and/or a reamed acetabular surface or glenoid surface. The virtual implant overhang, virtual implant oversizing, and/or virtual implant undersizing can be determined in relationship to an uncut and/or a cut proximal femur, an uncut and/or a cut proximal humerus.

Using, for example, a display and one or more computer processors generating the display, the surgeon and/or the computer processor can determine if portions of a virtual implant component are too small or "undersized" for the bone, e.g. uncut bone or bone prepared for accepting an implant. The bone can be prepared in a computer simulation to accept the bone, for example by simulating one or more of a bone cut, a drilling, a burring, a milling, a reaming, a broach and/or an impact and/or any other type of bone removal known in the art. If portions of a virtual implant component are too small or undersized for the bone, e.g. uncut bone or bone prepared for accepting an implant, in select areas, the amount of undersizing can be determined, for example as a distance measurement, e.g. in mm, or an area measurement. If a distance measurement is used, it can be, for example a maximum amount of bone not covered by the implant, e.g. uncut bone or bone prepared for accepting an implant, or an average amount of bone not covered by the implant, e.g. uncut bone or bone prepared for accepting an implant. If an area measurement is used, it can be a measurement, for example, in $mm^2$ indicating, for example, the total area of bone not covered by the implant, e.g. uncut bone or bone prepared for accepting an implant.

The overhang or undersizing analysis can be performed in subregions. The subregions can be selected, for example, based on clinical relevance. For example, a subregion identified as an area of potential soft-tissue impingement caused by implant overhang can be analyzed for the presence of implant overhang. The subregion analysis can, for example, be performed along an implant edge, and/or margin and/or perimeter. The subregion analysis can, for example, be performed along a bone edge, and/or margin and/or perimeter; which can be an unaltered bone or a bone prepared for accepting the implant, e.g. after a bone cut, a drilling, a milling, a burring, a reaming, a broaching and/or an impacting.

For example, in a knee replacement, a subregion analysis for implant overhang and/or undersizing of a femoral component can be performed in the trochlear region of the bone, the anterior third of the medial femoral condyle of the bone (on its inside and/or outside), the central third of the medial femoral condyle of the bone (on its inside and/or outside), the posterior third of the medial femoral condyle of the bone (on its inside and/or outside), the posterior aspect of the medial femoral condyle of the bone, the intercondylar notch region, the anterior third of the lateral femoral condyle of the bone (on its inside and/or outside), the central third of the lateral femoral condyle of the bone (on its inside and/or outside), the posterior third of the lateral femoral condyle of the bone (on its inside and/or outside), the posterior aspect of the lateral femoral condyle of the bone. The bone, e.g. the distal femur, can be an unaltered bone or a bone prepared for accepting the implant, e.g. after a bone cut, a drilling, a milling, a burring, a reaming, a broaching and/or an impacting.

For example, in a knee replacement, a subregion analysis for implant overhang and/or undersizing of a femoral component can be performed in the anterior flange region of an implant component, the anterior third of the medial femoral condyle of an implant component (on its inside and/or outside), the central third of the medial femoral condyle of an implant component (on its inside and/or outside), the posterior third of the medial femoral condyle of an implant component (on its inside and/or outside), the posterior aspect of the medial femoral condyle of an implant component, the intercondylar notch region, the anterior third of the lateral femoral condyle of an implant component (on its inside and/or outside), the central third of the lateral femoral condyle of an implant component (on its inside and/or outside), the posterior third of the lateral femoral condyle of an implant component (on its inside and/or outside), the posterior aspect of the lateral femoral condyle of an implant component.

For example, in a knee replacement, a subregion analysis for implant overhang and/or undersizing of a tibial component can be performed at the anterior medial aspect of the tibial plateau of the bone, anterior lateral aspect of the tibial plateau of the bone, medial aspect of the tibial plateau of the bone, lateral aspect of the tibial plateau of the bone, anterior center of the tibial plateau of the bone, posterior medial aspect of the tibial plateau of the bone, posterior lateral aspect of the tibial plateau of the bone, posterior central aspect of the tibial plateau of the bone, using, for example, the rim, edge, margin or perimeter of the tibial plateau of the bone, cut or uncut. The bone, e.g. the proximal tibia, can be an unaltered bone or a bone prepared for accepting the implant, e.g. after a bone cut, a drilling, a milling, a burring, a reaming, a broaching and/or an impacting.

For example, in a knee replacement, a subregion analysis for implant overhang and/or undersizing of a tibial component can be performed at the anterior medial aspect of the tibial component, anterior lateral aspect of the tibial component, medial aspect of the tibial component, lateral aspect of the tibial component, anterior center of the tibial component, posterior medial aspect of the tibial component, posterior lateral aspect of the tibial component, posterior central aspect of the tibial component, using, for example, the rim, edge, margin or perimeter of the tibial plateau of the bone, cut or uncut.

In some embodiments, a computer processor or a surgeon using a computer processor with a computer display, can place one or more virtual implant components using any of the parameters described in the specification, e.g. a mechanical axis alignment, a rotation alignment, a predetermined rotation, tibial slope, a femoral offset, a femoral component flexion, a femoral component position, e.g. to avoid anterior notching, a medial lateral joint line, a lateral joint line. Other parameters for placing an implant component relative to a bone or a cartilage can include a predetermined or desired medial gap, a predetermined or desired lateral gap, e.g. for different degrees of flexion and/or extension, an implant component alignment tangent to one or more articular surface(s), e.g. a medial femoral condyle and/or a lateral femoral condyle, e.g. for different degrees of flexion or extension, or a medial tibial plateau or a lateral tibial plateau. Other parameters for placing an implant component can include a kinematic analysis, for example using a kinematic simulation, for example simulating the relative movement of a femoral and/or a patellar component or the relative movement of a femoral and/or tibial component, e.g. during flexion or extension of a knee. In any of the embodiments, an implant placement can be performed with regard to one or more of a cortical bone, subchondral bone, cartilage, normal, damaged or diseased cartilage, an anatomic axis, a biomechanical axis. The placement of a virtual implant component can be performed using a single parameter or multiple parameters.

Following the placement of the virtual implant component, a computer processor or a surgeon assisted by a computer processor, for example with a computer display, can perform an analysis of implant fit evaluating, for example, implant overhang or undersizing as described in the specification. If the analysis of implant overhang or undersizing yields an undesirable result, e.g. a significant implant overhang with the potential for soft-tissue impingement or a significant implant undersizing with the potential for implant subsidence or both, the computer processor or the surgeon can select a different virtual implant component and repeat the analysis. Alternatively and/or in addition, the computer processor and/or surgeon can change the position, and/or orientation and/or alignment of the implant component with regard to any of the foregoing parameters, e.g. one or more parameters used for the placing of the virtual implant component, in order to achieve an improved implant fit (e.g. with less overhang and/or less undersizing) and the analysis of implant fit evaluating, for example, implant overhang or undersizing can be repeated. For example, the computer processor or the surgeon can optionally change an implant rotation and/or an implant flexion and/or an implant slope or the computer processor can change an implant component position and/or orientation based on a kinematic measurement or simulation, showing, for example, motion conflict between a virtual femoral and a virtual tibial component, e.g. with the femoral component "diving" into the tibial component.

The placement of one or more virtual implant components and assessment of implant fit to the bone and/or cartilage can be performed automatically, for example wherein a computer processor automatically determines the best fitting implant component, e.g. with the least amount of implant overhang and/or undersizing using, for example, any of the foregoing parameters. For example, the computer processor can optionally evaluate all virtual implant components available in one or more implant component libraries to determine the best fitting implant component.

The one or more analyses of implant fit, e.g. involving assessment of implant overhang or undersizing, can be performed manually, e.g. using a user interface, semi-automatically, or automatically, e.g. using one or more computer processors and/or one or more user interfaces.

The one or more templates, virtual implants, images, 3D models of implants, 3D bone models, libraries of virtual implants, virtual surgical plans can be stored on computer storage media, e.g. a CD ROM, a hard disk, RAM, and other means of data storage and can be retrieved or processed using a computer processor.

Scoring, Risk Assessment

The measurements of implant overhang or undersizing, including any subregion analysis, can be performed as a linear, e.g. distance measurement, an area measurement and/or a volume measurement. For example, the total volume of the portions of an implant component that are overhanging a cut bone can be determined.

In some embodiments, one or more measurements of implant overhang or undersizing can be normalized. For example, a linear or area measurement of implant overhang or undersizing can be normalized relative to an area of bone exposed for implantation or cut for implantation, e.g. in a virtual surgical plan. For example, a distance or area measurement of implant overhang can be normalized relative to a perimeter of soft-tissue envelope present around the bone, or a perimeter, edge or margin of the cut bone, e.g. in a subregion or around the entire cut bone, e.g. a distal femur. A distance or area measurement of implant undersizing can be normalized to an area or volume of cut bone in a virtual surgical plan. For example, in a tibial component placement, the amount, e.g. in distance (e.g. mean, minimum, maximum) or area of virtual cut bone not covered by a virtual implant component can be determined and can be divided by the total area of the virtually cut bone surface for placing the virtual tibial component to derive a normalized value for the total area of cut bone surface.

Optionally, any of the measurements of implant overhang or undersizing can be normalized to bone size, measured, for example, in a non-limiting matter, as maximum bone perimeter, bone area or bone volume or resection volume. Optionally, any of the measurements overhang or undersizing can be normalized to resection depth, resection area and/or resection volume.

The determination and/or measurement of implant overhang and/or undersizing can be automatic, semi-automatic, and/or manual using, for example, one or more computer processors and/or a computer display and/or using an artificial neural network and/or an artificial intelligence system. Virtual implant component overhang, oversizing and/or undersizing can be measured in relationship to at least one anatomic structure by at least one computer processor. Virtual implant component overhang, oversizing and/or undersizing can be highlighted visually, e.g. using color coding, e.g. red for overhang over an anatomic structure. Virtual implant component overhang, oversizing and/or undersizing can be expressed in numeric values, by at least one computer processor, e.g. in mm, $mm^2$, or $mm^3$.

An implant component overhang score can be derived. An implant component undersizing score can be derived. An implant component overhang score or undersizing score can be, for example, the sum of all implant component overhang or undersizing, e.g. in mm, mm$^2$, mm$^3$, from all subregions in which an implant component overhang or undersizing was detected. Any mathematical or statistical method or function known in the art can be used to derive an implant component overhang or undersizing score. Optionally, measurements from different subregions can be given a different weight, for example based on clinical risk in a given subregion, e.g. of developing postoperative pain.

An implant component overhang or undersizing score can be correlated with one or more clinical outcome measurements, e.g. a soft-tissue impingement and/or pain or an implant component subsidence and/or pain. An implant component overhang or undersizing score can be used, by at least one computer processor, to compute a risk of developing postoperative pain.

Mathematical functions and/or statistical functions or methods can be applied to derive or determine a risk associated for a given overhang or undersizing score for a clinical outcome. For example, the risk associated with an implant component overhang score for developing soft-tissue impingement and/or postoperative pain can be determined and can be expressed using a statistical term or method, e.g. an odds ratio. The risk associated with an implant component undersizing score for developing implant subsidence and/or postoperative pain and/or implant failure can be determined and can be expressed using a statistical term or method, e.g. an odds ratio. A risk, e.g. a risk for postoperative pain or limitations in postoperative function, can be determined by one or more computer processors using any of the embodiments described in the specification.

EXAMPLES

In a non-limiting example, a CT scan of the knee of a patient scheduled for joint replacement can be obtained. The CT scan can include slices or images through the hip joint and the ankle joint. A computer processor can determine the center of the femoral head and the center of the ankle joint, e.g. by determining the center of a sphere fitted into the femoral head and by determining the mid-point connecting the medial and the lateral malleolus. The computer processor can then compute the mechanical axis of the leg as the axis connecting the center of the hip joint with the center of the ankle joint. The computer processor can segment the bone surface of the distal femur and the proximal tibia and the computer processor can determine the center of the distal femur, e.g. as the geometric center point at the intersect of a first line connecting the most medial point of the medial epicondyle and the most lateral point of the lateral epicondyle and a second line perpendicular to the first line tangent with at least portions of the roof of the intercondylar notch and substantially equidistant to the medial and the lateral wall of the intercondylar notch for the center point of the distal femur. The center point of the proximal tibial can, for example, be computed by the computer processor as the mid-point between the medial and the lateral tibial spine. The computer processor can then compute the axis connecting the center point of the hip/femoral head and the center point of the distal femur which yields the femoral mechanical axis. The computer processor can then compute the axis connecting the center of the ankle to the center point of the proximal tibia which yields the tibial mechanical axis. The angle between the femoral mechanical axis and the mechanical axis of the leg and/or the angle between the tibial mechanical axis and the mechanical axis of the leg can be used by the computer processor to compute a varus or valgus correction for a femoral and/or tibial implant component to place the femoral and/or tibial virtual implant component in neutral mechanical axis alignment.

The computer processor can then determine at least one of a coordinate, a peripheral margin, a dimension, a shape, a radius, a convexity, a concavity of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau surface, a lateral tibial plateau surface, a medial tibial plateau surface, a lateral tibial plateau surface, any of the foregoing tissues and/or structures on a surgically exposed surface, any of the foregoing tissues and/or structures in a subsurface location. Optionally, the computer processor can, for example, determine a distance between the most medial point of a medial epicondyle and the most lateral point of a lateral epicondyle, the most anterior point of a trochlea, one or more coordinates of a cortex superior to the trochlea and the most posterior point of the medial condyle and/or the most posterior point of the lateral condyle; the respective distances between these points and/or their respective coordinates can be used to measure distances for selecting, for example, a virtual implant (femoral and/or tibial) from a virtual library of implants that most closely approximates with its corresponding dimensions, i.e. a mediolateral implant width or an anteroposterior implant width). The virtual implant can be placed by the computer processor aligned relative to at least one of an anatomic structure, an anatomic landmark, a mechanical axis of a leg, a mechanical axis of a femur, a mechanical axis of a tibia, a Whiteside's line, a transepicondylar line, a rotation axis of a femur, a rotation axis of the tibia, an anatomic axis of the femur, an anatomic axis of the tibia, a biomechanical axis of the patella, a rotation axis of the patella, an anatomic axis of the patella, an abduction axis or line, e.g. on the contact surface of two opposing articular surfaces, an adduction axis or line, e.g. on the contact surface of two opposing articular surfaces, a transepicondylar line, a Whiteside's line, a femoral, tibial, patellar contact surface or combinations thereof, a femoral, tibial, patellar contact line, or combinations thereof, a medial joint line, a lateral joint line, a tibial slope, a tibial offset, a tibial plateau dimension, a tibial plateau perimeter, a dimension, a perimeter, a surface, a volume of a cut tibial plateau, an anterior margin of a tibial plateau (before and/or after a bone removal, e.g. a bone cut or a burring), a posterior margin of a tibial plateau (before and/or after a bone removal, e.g. a bone cut or a burring), a medial margin of a tibial plateau (before and/or after a bone removal, e.g. a bone cut or a burring), a lateral margin of a tibial plateau (before and/or after a bone removal, e.g. a bone cut or a burring), a femoral condyle offset, a femoral condyle, a trochlea, a distal femoral dimension, a posterior femoral dimension, a femoral perimeter, e.g. a perimeter of a femoral condyle, a dimension, a perimeter, a surface, a volume of a cut distal femur, e.g. a cut femoral condyle or a trochlea, a medial, inferior, lateral, superior, anterior, posterior margin of a cut distal femur, e.g. a posterior femoral condyle, a dimension, an anterior femoral cortex, e.g. to avoid notching of a femoral component, a perimeter, a surface, a volume of an uncut or a cut or milled patella, a shape of a medial patellar facet, a shape of a lateral patellar facet, a shape of a patella, a trochlear sulcus, a trochlear sulcus line, a depth of a trochlear sulcus, a trochlear height, e.g. for assessing the fit, size, and/or shape of an anterior flange of a femoral component, a radius, a curvature, a shape of an articular surface, e.g. a femoral condyle, a tibial plateau, a patella, at least a portion of an internal or external margin, periphery, edge, perimeter, anteroposterior, mediolateral, oblique dimension, diameter, radius, curvature, geometry, shape or surface of one or more structures of a physical joint, e.g. a cortical bone, subchondral bone, cartilage, damaged or diseased cartilage, or combination thereof.

With the femoral and/or tibial implant component selected and aligned in this exemplary, non-limiting manner by the computer processor, the computer processor can determine, for example, the distance between

- A medial edge of the virtual tibial component and the medial edge of the cut tibial plateau
- A lateral edge of the virtual tibial component and the lateral edge of the cut tibial plateau
- A posterior edge of the medial aspect of the virtual tibial component and the posterior edge of the cut medial tibial plateau
- A posterior edge of the lateral aspect of the virtual tibial component and the posterior edge of the cut lateral tibial plateau
- A medial edge of the medial condylar portion of the virtual femoral component and the medial edge of the cut medial femoral condyle
- A lateral edge of the lateral condylar portion of the virtual femoral component and the lateral edge of the cut lateral femoral condyle
- A posterior edge of the medial posterior condylar portion of the virtual femoral component and the posterior edge of the posterior portion of the cut medial femoral condyle
- A posterior edge of the lateral posterior condylar portion of the virtual femoral component and the posterior edge of the posterior portion of the cut lateral femoral condyle
- An anterior flange (corresponding to the anterior femoral cut) of the virtual femoral component and an anterior cortex superior to the trochlea The computer processor can then classify the foregoing exemplary measurements as overhang based on the coordinate information of the virtual implant structures or features, e.g. a medial edge of the virtual implant, and the coordinate information of the anatomic structures. For example, if the coordinate(s) of a virtual implant structure or feature are located outside the perimeter coordinates of a cut distal femur or a cut proximal tibia, the computer processor, and optionally a discriminative artificial neural network, can classify the coordinates of the virtual implant structure or feature as overhanging or oversized. For example, if the coordinate(s) of a virtual implant structure or feature are located inside the perimeter coordinates of a cut distal femur or a cut proximal tibia, the computer processor, and optionally a discriminative artificial neural network, can classify the coordinates of the virtual implant structure or feature as undersized. The computer processor can determine the distance or difference between coordinates of the virtual implant structure or features and the anatomic structure(s). The distance or difference can be expressed as a distance measurements and/or an area measurement, e.g. area of virtual implant structure and/or feature outside the coordinates of the perimeter of a cut distal femur or proximal tibia. The computer processor can then perform a pixel count of virtual implant structure or features outside or inside the coordinates of the perimeter of a cut distal femur or proximal tibia; with the pixel size known, for example, from the imaging study, the computer processor can determine the area of virtual implant component overhang/oversizing and/or undersizing. If volumetric measurements are performed, the computer processor can then perform a voxel count of virtual implant structure or features outside or inside the coordinates of the cut distal femur or proximal tibia; with the voxel size known, for example, from the imaging study, the computer processor can determine the volume of virtual implant component overhang/oversizing and/or undersizing, for example along multiple cut surfaces of the distal femur.

The measurements of implant overhang or undersizing, including any subregion analysis, can be performed by the computer processor, and optionally an ANN, as a linear, e.g. distance measurement, an area measurement and/or a volume measurement. For example, the total volume of the portions of an implant component that are overhanging a cut bone can be determined.

Optionally, the computer processor can normalize any of the measurements of implant overhang or undersizing to bone size, measured, for example, in a non-limiting matter, as maximum bone perimeter, bone area or bone volume, or resection volume. Optionally, any of the measurements overhang or undersizing can be normalized to resection depth, resection area and/or resection volume.

Optionally, the computer processor or ANN can derive an implant component overhang score, oversizing score, or undersizing score. An implant component overhang score or undersizing score can be, for example, the sum of all implant component overhang or undersizing, e.g. in mm, $mm^2$, $mm^3$, from at least a portion of or all subregions in which an implant component overhang or undersizing was detected by the computer processor. Any mathematical or statistical method or function known in the art can be used to derive an implant component overhang or undersizing score. Optionally, measurements from different subregions can be given a different weight, for example based on clinical risk in a given subregion, e.g. of developing postoperative pain.

An implant component overhang or undersizing score can be correlated by at least one computer processor with one or more clinical outcome measurements, e.g. a soft-tissue impingement and/or pain or an implant component subsidence and/or pain. An implant component overhang or undersizing score can be used, by at least one computer processor, to compute a risk of developing postoperative pain. The risk of developing postoperative pain can be expressed in various statistical measures or terms, e.g. an odds ratio or other statistical terms or tools known in the art.

An implant component overhang or undersizing score can be classified by at least one discriminative ANN based on one or more clinical outcome measurements, e.g. a soft-tissue impingement and/or pain or an implant component subsidence and/or pain, e.g. no postoperative pain, mild postoperative pain, moderate postoperative pain or several postoperative pain, captured, for example, using patient reported outcome measurements such as the WOMAC score, SF-12, SF-36, Knee Society Score, Oxford Score. An implant component overhang or undersizing score can be used, by the ANN, to predict a risk of developing postoperative pain. The risk of developing postoperative pain can be expressed in various statistical measures or terms, e.g. an odds ratio or other statistical terms or tools known in the art.

The foregoing example in a patient undergoing knee replacement can be readily applied to hip replacement, shoulder joint replacement or ankle joint replacement, e.g. by using CT scan or MRI scan data or other scan data and anatomic structures corresponding to the particular joint and virtual implant components from a library of virtual implants for the particular joint.

The term "cut", e.g. cut tibial plateau or cut femoral condyle, used throughout the specification is a virtual cut generated by the computer processor based on the imaging data of the patient and/or based on the geometry of a virtual implant component.

In any of the embodiments, the at least one computer system can be the same or different. In any of the embodiments, the at least one processor can be the same or different.

In any of the embodiments, a computer system including one of more of the processors can include a logic subsystem and a data holding subsystem, which can be the same or different. The computer system can optionally include a display subsystem, a communication subsystem, and/or other components. The computer system can include user input devices such as keyboards, mice, game controllers, cameras, microphones, touch screens, gesture and/or voice recognition devices. Logic subsystems can include one or more physical devices configured to execute one or more instructions. For example, logic subsystems can be configured to execute one or more instructions that are part of one or more artificial neural networks, machine learning systems, deep learning systems, applications, services, programs, routines, libraries, classification systems, objects, components, data structures, or other logical constructs. Such instructions may be implemented to perform a task, implement a data type, perform a classification, transform the state of one or more devices, generate a treatment plan, select a treatment plan, modify a treatment plan, generate a virtual surgical plan, select a virtual surgical plan, modify a virtual surgical plan, generate a virtual display, or otherwise arrive at a desired result. Logic subsystems can include one or more processors that can be configured to execute software instructions or algorithms. Additionally or alternatively, logic subsystems can include one or more hardware or firmware logic machines configured to execute hardware or firmware instructions. Processors of logic subsystems can be single core or multicore, and the programs executed thereon may be configured for parallel or distributed processing. Logic subsystems can optionally include individual components that can be distributed throughout two or more devices, which can optionally be located locally or remotely and/or can be configured for coordinated processing. One or more aspects of logic subsystem can be virtualized and executed by remotely accessible networked computer devices configured, for example, in a cloud computing configuration. A data-holding subsystem can include one or more physical, non-transitory, devices configured to hold data and/or instructions executable by logic subsystem to implement the methods and processes described in the specification.

When such methods and processes are implemented, the state of data-holding subsystem can be transformed or modified, e.g. to hold different data. Data-holding subsystems can include removable media and/or built-in devices. Data-holding subsystems can include optical memory devices (e.g. CD, DVD, HD-DVD, Blu-Ray Disc, etc.), semiconductor memory devices (e.g. RAM, EPROM, EEPROM, etc.) and/or magnetic memory devices (e. g. hard disk drive, floppy diskdrive, tape drive, MRAM, etc.), among others. Data-holding subsystems can include devices with one or more of the following characteristics: volatile, nonvolatile, dynamic, static, read/write, read-only, random access, sequential access, location addressable, file addressable, and content addressable. In some embodiments, logic subsystems and data-holding subsystems can be integrated into one or more common devices, such as an application specific integrated circuit or a system on a chip. Data-holding subsystems can be in the form of removable computer-readable storage medium or media, which can be used to store and/or transfer data and/or instructions executable to implement the methods and processes described throughout the specification. Removable computer-readable storage media can be CDs, DVDs, HD-DVDs, Blu-Ray Discs, EEPROMs, and/or floppy disks, among others. Data-holding subsystems can include one or more physical, non-transitory devices. Aspects of the instructions described in the specification can be propagated in a transitory fashion by a pure signal (e.g. an electromagnetic signal, an optical signal, etc.) that is not held by a physical device for at least a finite duration. Data and/or other forms of information pertaining to the present disclosure may be propagated by a pure signal. The terms "module", "program", and "engine" can be used to describe an aspect of a computer system that can be implemented to perform one or more particular functions. A module, program, or engine can be initiated via a logic subsystem executing instructions held by data-holding subsystem. Different modules, programs, and/or engines can be initiated from the same or from different applications, services, code blocks, objects, libraries, routines, API's, functions, etc. The terms "module", "program", and "engine" are meant to encompass individual or groups of executable files, data files, libraries, drivers, scripts, database records, etc. A service can be an application program executable across multiple user sessions and available to one or more system components, programs, and/or other services. A service can run on a server responsive to a request from a client. A display subsystem can optionally be used and can be used to present a visual representation of data held by a data-holding subsystem. Methods and processes can change the data held by a data-holding subsystem, and thus change the state of the data-holding subsystem. The state of a display subsystem can likewise be transformed to visually represent changes in the underlying data. Display subsystems can include one or more display devices utilizing virtually any type of technology. Such display devices can be combined with logic subsystems and/or data-holding subsystems in a shared enclosure, or such display devices can be peripheral, e.g. standalone, display devices. When included, a communication subsystem can be configured to communicatively couple one or more computer systems. A communication subsystem can include wired and/or wireless communication devices compatible with one or more different communication protocols. As nonlimiting examples, the communication subsystem can be configured for communication via a wireless telephone network, a wireless local area network, a wired local area network, a wireless wide area network, a wired wide area network, etc. A communication subsystem can allow a computer system to send and/or receive messages to and/or from other devices via a network, e.g. an internal or an external network.

The invention claimed is:

1. A system for fitting, aligning, or fitting and aligning a virtual implant component for a joint replacement in a patient comprising:
at least one computer system comprising at least one processor,
wherein the at least one processor is configured to receive imaging data of the joint of the patient,
wherein the imaging data comprises at least one image of at least a portion of a surface of the joint, wherein the imaging data comprises a CT scan, an MRI scan, an ultrasound scan, data generated based on one, two or more x-rays or combinations thereof of the joint,
wherein the at least one processor is configured to generate a three-dimensional (3D) model of the at least a portion of the surface of the joint based on the imaging data,
wherein the at least one processor is configured to access electronic data of a virtual implant component, the virtual implant component comprising a shape associated with a physical implant component,
wherein the at least one processor is configured to use an artificial neural network to fit, align, or fit and align the virtual implant component in relationship to the 3D model of the at least a portion of the surface of the joint, and
wherein the at least one processor is configured to use the artificial neural network to fit, align, or fit and align the virtual implant component in relationship to the at least a portion of the surface the joint, an anatomic structure, an anatomic axis, a biomechanical axis, a mechanical axis, a rotation axis, a predetermined angle, a version, a slope, a joint line, or a combination thereof.

2. The system of claim 1, wherein the at least one processor is configured to use the artificial neural network to select the virtual implant component from a library of virtual implant components, wherein the library of virtual implant components comprises at least two virtual implant components, wherein the at least two virtual implant components have different shapes.

3. The system of claim 2, wherein the at least one processor is configured to use the artificial neural network to select the virtual implant component based on the fit, the alignment, or the fit and the alignment of the virtual implant component.

4. The system of claim 2, wherein the virtual implant components are stored in STL file format in the library of virtual implant components.

5. The system of claim 1, wherein the at least a portion of the surface of the joint comprises a cartilage surface, a subchondral bone surface, a cortical bone surface, or a combination thereof.

6. The system of claim 1, wherein the at least a portion of the surface of the joint comprises an uncut bone surface, or wherein the at least a portion of the surface of the joint comprises a cut bone surface.

7. The system of claim 6, wherein the cut bone surface comprises at least a portion of a margin, an edge, a perimeter or a combination thereof of the cut bone surface.

8. The system of claim 1, wherein the at least one processor is configured to use the artificial neural network to fit, align, or fit and align the virtual implant component in relationship to at least one margin of a cut bone surface, edge of a cut bone surface, perimeter of a cut bone surface, inclination, predetermined resection plane, or a combination thereof.

9. The system of claim 1, wherein the at least one processor is configured to use the artificial neural network to fit, align, or fit and align the virtual implant component using a range of motion measurement, a curvature analysis, a kinematic measurement, a kinematic simulation or a combination thereof.

10. The system of claim 1, wherein the at least one processor is configured to use the artificial neural network to fit, align, or fit and align the virtual implant component using a soft-tissue impingement analysis.

11. The system of claim 1, wherein the at least one processor is configured to use the artificial neural network to fit, align, or fit and align the virtual implant component based on one or more CT images, MR images, x-ray images, ultrasound images, PET images, SPECT images, nuclear scintigraphy images, thermography images, wearable device data, IMU data, patient history, clinical assessments, patient reported outcome measurements, range of motion measurements, clinical scores, function scores, objective outcome measurements, subjective outcome measurements or a combination thereof.

12. The system of claim 1, wherein the computer processor is configured to determine at least one measure of fit, alignment, or fit and alignment, wherein the at least one measure comprises one or more numeric distance value, surface area value, volume value, angle measurement value or a combination thereof.

13. The system of claim 1, wherein the at least one processor is configured to fit and/or align and/or select the virtual implant component so as to minimize an overhang, oversizing or overhang and oversizing in relationship to the at least a portion of the surface of the joint, the at least one anatomic structure, a cut bone surface, a margin of a cut bone surface, an edge of a cut bone surface, a perimeter of a cut bone surface, or a combination thereof.

14. The system of claim 1, wherein the at least one processor is configured to fit and/or align and/or select the virtual implant component so as to minimize an undersizing in relationship to the at least a portion of the surface of the joint, the at least one anatomic structure, a cut bone surface, a margin of a cut bone surface, an edge of a cut bone surface, a perimeter of a cut bone surface, or a combination thereof.

15. The system of claim 1, wherein the joint is a knee joint and wherein the at least one processor is configured to use the artificial neural network to fit, align, or fit and align the virtual implant component in relationship to at least a peripheral margin, a bone edge, a dimension, a plane, a shape, a radius, a convexity, a concavity, or a surface of at least one of a medial wall of the femoral notch, a lateral wall of the femoral notch, a roof of the femoral notch, a residual ACL origin, a residual ACL insertion, a medial wall of the medial condyle, a lateral wall of the lateral condyle, a medial epicondylar eminence, a lateral epicondylar eminence, a medial femoral condyle, a lateral femoral condyle, a posterior portion of medial femoral condyle, a posterior portion of lateral femoral condyle, a central portion of medial femoral condyle, a central portion of lateral femoral condyle, an anterior portion of medial femoral condyle, an anterior portion of lateral femoral condyle, an intercondylar notch, an intercondylar notch surface, an intercondylar notch ceiling, an intercondylar notch medial wall, an intercondylar notch lateral wall, a posterior portion of medial tibial plateau, a posterior portion of lateral tibial plateau, a central portion of a medial tibial plateau, a central portion of a lateral tibial plateau, an anterior portion of medial tibial plateau, an anterior portion of lateral tibial plateau, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, an uncut medial tibial plateau surface, an uncut lateral tibial plateau surface, a cut medial tibial plateau surface, a cut lateral tibial plateau surface, an uncut femoral condyle surface, a cut femoral condyle surface, an uncut anterior femur surface, a cut anterior femur surface, a transepicondylar axis, a Whiteside's line, an anterior cortex, a tibial slope, a medial joint line, a lateral joint line or a combination thereof.

16. The system of claim 1, wherein the joint is a hip joint and wherein the at least one processor is configured to use the artificial neural network to fit, the align, or fit and align the virtual implant component in relationship to at least a peripheral margin, a bone edge, a dimension, a plane, a shape, a radius, a convexity, a concavity or a surface of at least one of a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a fovea capitis, a transverse acetabular ligament, a pulvinar, a ligamentum teres, a labrum, one or more osteophytes, a femoral neck angle, a femoral shaft angle, an acetabular angle, an inclination, an acetabular anteversion, a femoral anteversion, a femoral shaft angle, a pelvic tilt, a pelvic plane, a femoral offset, a Shenton's line, a Hilgenreiner line, a Perkin line, an acetabular index, a femoral resection plane, an acetabular resection plane, an uncut femoral surface, a cut femoral bone surface, or a combination thereof.

17. The system of claim 1, wherein the joint is a shoulder joint and wherein the at least one processor is configured to use the artificial neural network to fit, the align, or fit and align the virtual implant component in relationship to a peripheral margin, a bone edge, a dimension, a plane, a shape, a radius, a convexity, a concavity, or a surface of at least one of a portion of or an entire glenoid, a portion of or an entire coracoid process, a portion of or an entire acromion, a portion of a clavicle, a portion of or an entire humeral head, a portion of or an entire humeral neck, a portion of a humeral shaft, one or more humeral osteophytes, one or more glenoid osteophytes, a portion of or an entire glenoid labrum, a portion of or an entire shoulder ligament, a portion of a shoulder capsule, a humeral neck angle, a humeral shaft angle, a glenoid angle, a glenoid inclination, a glenoid anteversion, a humeral anteversion, a humeral shaft angle, a humeral offset, a humeral resection plane, a glenoid resection plane, an uncut humeral surface, a cut humeral bone surface, or a combination thereof, or wherein the joint is an ankle joint and wherein the at least one processor is configured to use the artificial neural network to fit, the align, or fit and align the virtual implant component in relationship to at least a peripheral margin, a bone edge, a dimension, a plane, a shape, a radius, a convexity, a concavity or a surface of at least one of a portion of or an entire distal tibia, a portion of or an entire distal fibular, a portion of or an entire talus, one or more tibial or fibular osteophytes, one or more talar osteophytes, a portion of or an entire ankle ligament, a portion of an ankle joint capsule, a tibial angle, a fibular angle, a talar angle, a tibial resection plane, a talar resection plane, an uncut tibial surface, an uncut talar surface, a cut tibial bone surface, a cut talar bone surface, or a combination thereof.

18. The system of claim 1, wherein the artificial neural network is a discriminative artificial neural network or a generative neural network.

19. The system of claim 1, wherein the at least one processor is configured to determine a score of virtual implant oversizing, implant overhang, implant undersizing, implant fit, implant alignment or a combination thereof in relationship to the at least a portion of the surface of the joint, the anatomic structure, the anatomic axis, the biomechanical axis, the mechanical axis, the rotation axis, the predetermined angle, the version, the slope, the joint line, a cut bone surface, a margin of a cut bone surface, an edge of a cut bone surface, a perimeter of a cut bone surface, or a combination thereof.

20. The system of claim 1, wherein the at least one processor is configured to compute a risk of developing postoperative pain based on the fit, alignment, or fit and alignment of the virtual implant component.

21. The system of claim 1, wherein the at least one processor is configured to determine a virtual implant component overhang, virtual implant component oversizing, virtual implant component undersizing, virtual component implant fit, virtual implant component alignment or combinations thereof in numeric values, and wherein the numeric values comprise at least one of mm, $mm^2$, $mm^3$, an angular measurement or a combination thereof.

22. The system of claim 1, wherein the joint is a knee joint and wherein the at least one processor is configured to align the virtual implant component in relationship to the 3D model based at least in part on a transepicondylar axis, a Whiteside's line, a femoral bone surface, a femoral condyle surface, a femoral offset, a femoral component flexion, an anterior cortex, a tibial plateau surface, a tibial slope, a medial joint line, a lateral joint line, a cartilage surface, a bone surface, or a combination thereof.

23. The system of claim 1, wherein the joint is a hip joint and wherein the at least one processor is configured to align the virtual implant component in relationship to the 3D model based at least in part on a femoral neck angle, a femoral shaft angle, an acetabular angle, an acetabular anteversion, a femoral anteversion, an inclination, a femoral shaft angle, a pelvic tilt, a pelvic plane, a Shenton's line, a Hilgenreiner line, a Perkin line, an impingement analysis, a cartilage surface, a bone surface or a combination thereof.

24. The system of claim 1, wherein the joint is a shoulder joint and wherein the at least one processor is configured to align the virtual implant component in relationship to the 3D model based at least in part on a glenoid version, a humeral version, a cartilage surface, a bone surface or a combination thereof.

25. The system of claim 1, wherein the joint is an ankle joint and wherein the at least one processor is configured to align the virtual implant component in relationship to the 3D model based at least in part on a tibial angle, a fibular angle, a talar angle, a tibial resection plane, a talar resection plane, an uncut tibial surface, an uncut talar surface, a cut tibial bone surface, a cut talar bone surface, a cartilage surface, a bone surface or a combination thereof.

26. The system of claim 1, wherein the at least one processor is configured to generate a treatment plan based on the fit, alignment or fit and alignment of the virtual implant component in relationship to the 3D model, wherein the treatment plan comprises coordinate information of a bone facing surface of the virtual implant component.

27. The system of claim 1, wherein the at least one processor is configured to register at least a portion of the coordinate information of the bone facing surface of the virtual implant component with the patient.

* * * * *